(12) United States Patent
Diehn et al.

(10) Patent No.: US 7,193,135 B2
(45) Date of Patent: Mar. 20, 2007

(54) ROOT-PREFERRED, WOUND- AND INSECT-INDUCIBLE 2-OXOGLUTARATE-DEPENDENT OXYGENASE PROMOTER FROM MAIZE AND ITS USE

(75) Inventors: Scott Diehn, West des Moines, IA (US); Albert L. Lu, Newark, DE (US); Billy F. McCutchen, Clive, IA (US); Lynne E. Sims, Polk City, IA (US); Kim R. Ward, Bear, DE (US)

(73) Assignees: Pioneer Hi-Bred International, Inc., Johnston, IA (US); E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 11/299,452

(22) Filed: Dec. 12, 2005

(65) Prior Publication Data
US 2006/0137035 A1 Jun. 22, 2006

Related U.S. Application Data

(60) Provisional application No. 60/636,890, filed on Dec. 17, 2004.

(51) Int. Cl.
*C12P 7/62* (2006.01)
*C12P 11/00* (2006.01)
*C07H 21/04* (2006.01)
*A01H 1/00* (2006.01)

(52) U.S. Cl. .................... 800/295; 435/6; 435/69.1; 435/320.1; 435/410; 435/419; 435/468; 530/350; 530/370; 536/23.1; 536/24.1; 800/278; 800/287; 800/312

(58) Field of Classification Search ............. 800/295, 800/278, 287, 312; 435/6, 69.1, 320.1, 410, 435/419, 468; 530/350, 370; 536/23.1, 536/24.1
See application file for complete search history.

(56) References Cited

U.S. PATENT DOCUMENTS 5,633,363 A 5/1997 Colbert et al.

FOREIGN PATENT DOCUMENTS

| WO | WO 95/14098 | 5/1995 |
| WO | WO 99/10500 | 3/1999 |
| WO | WO 99/41391 | 8/1999 |
| WO | WO 2004/013169 A1 | 2/2004 |

OTHER PUBLICATIONS

Birren et al, Gen EMBL database Accession No. AC148152, Direct Submission Jun. 16, 2004.*
Birren, et al., Zea mays clone ZMM BBc0388A01, Database EMBL [Online], Accession No. AC148152, XP002384920.

\* cited by examiner

*Primary Examiner*—Phuong T. Bui
*Assistant Examiner*—Brendan O. Baggot
(74) *Attorney, Agent, or Firm*—Pioneer Hi-Bred International, Inc.

(57) ABSTRACT

The present invention provides compositions and methods for regulating expression of heterologous nucleotide sequences in a plant. Compositions include a novel nucleotide sequence for an inducible promoter for the gene encoding a maize 2-oxoglutarate-dependent oxygenase. A method for expressing a heterologous nucleotide sequence in a plant using the promoter sequences disclosed herein is provided. The method comprises stably incorporating into the genome of a plant cell a nucleotide sequence operably linked to the root-preferred promoter of the present invention and regenerating a stably transformed plant that expresses the nucleotide sequence.

30 Claims, 3 Drawing Sheets

Figure 1: 2OD Oxygenase Gene Expression is Up-regulated by Corn Rootworm Feeding
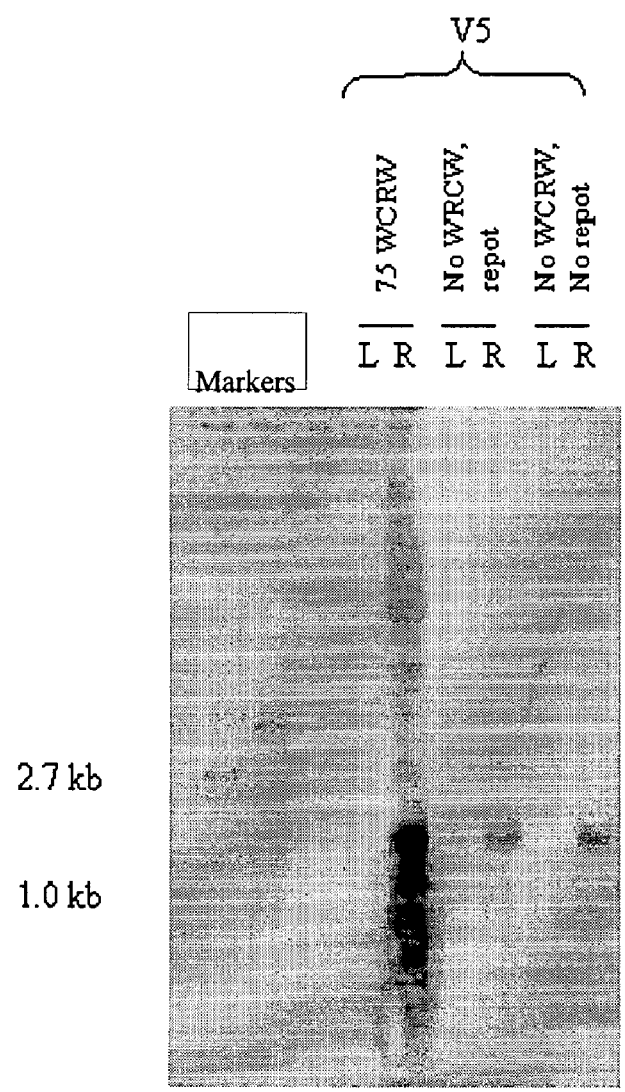

Figure 2: Wounding Time Course of 2OD Oxygenase Expression
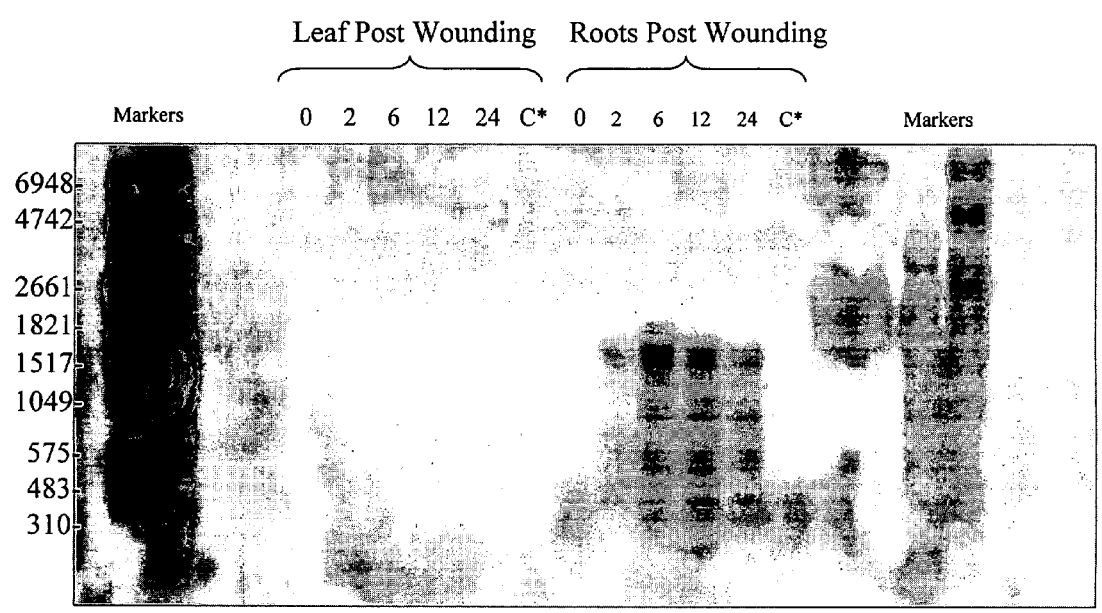

Figure 3: 2OD Oxygenase Promoter and 5'UTR

```
   1  GTCGACATGT CACGTTATCA ATGTAGAGAC TGATAAAAAT TTGACTCTGT
  51  TTCGTGAAAG TTGACATGCA CTATGTGTAG AAACCTAGCC GGCCTTCACA
 101  TGAAATCATA AAACTTCTAC GGAGGTCGGC TAGGTTTGTA TACACAACAC
 151  TCGACAAAGA AGGCATATCT GGAAACCGAT ATGGCTTTTT TTTATAAGTG
 201  TTGTAGTCCT GACACTCGAC AAAGAAGCTC CATTTGCCGA GTGCCTCCCA
 251  GCACACTTGG CAAAGTGACT GGCAAAGGGG CCCACTATTG CCCCCTTTGT
 301  CGAGAGTGCC AGGCTGGCAG TCACTCGACA AAGATGCTCC CTTTGCCAAG
 351  TGTCAATTGC GGCTCTCGGC ACAAAGGCTG TCGTGGGGGC CCACTGGAGC
 401  CTTATTTGCC GAGTGTCACG CCAGCAGGCA CTCGATAAAG GCTTCCTTTT
 451  TGCCGAGTGC CATTGAGGAC ACTCGACATA GTCTCTGTCA CCATCACTTG
 501  TCGCTGTCAC GGCAATTTTT CTTTGCCGAG CACTAGGGGA CACTTGGTAA
 551  AGACTTTGCC GAGTGTCCGA CATAATGCTA TCGGTAAAGA GGTCGTTGCT
 601  GATGTACAGT TCACTGAGTC CTTTTTACTA AGTGTCACAC TCGACAAAGA
 651  GTTTGTTGAG TGTTTTTTAG GCTTTGCCGA GTGCTTGCGA CACTCGGCAA
 701  AGCAGTATGT TTTGGTAGTG AGGTCGTTGT CGATAAACAG TTCACCGATC
 751  CCTATTTGCC GAATGCTACA CTCGAAGTGC CGCAGGCACT CGGGAAAGAA
 801  CCCTGTTTCG GTTGTGACTT GGTATTGTTA GGCTGTGTAT TGAATCCAAT
 851  GCTATCACAT TAGATATAAA CTAGATAACC GCGTATACAG TGTTTTATTC
 901  GATAAAACTC TACCCTCTCC TATGAAACTG TCTCTATATC TTTCCTCTTA
 951  ATTACAGTCA TGTTCCGCAC ATGATGCTGT ATCACCGCAC ATGGAGAGAG
1001  AGAAAAATAG ATTGGTCAGG CTGTTTGTAT ATGCAAGGCC TACGCTTCTA
1051  TTTAAGACC GTATCGTGGT TGCAGGCAGA AGCACACAAG CTAGCAATTG
                                         | (+1) TSS
1101  AAAAAAAAAA CAGGCA
```

The <u>TATA box</u> is shown in bold, underlined text.

TTGAC – Two "W-box" elements are shown in bold text.

The transcriptional start site (TSS), mapped by 5' RACE, is indicated at position 1084 by an "A" in a box.

ROOT-PREFERRED, WOUND- AND INSECT-INDUCIBLE 2-OXOGLUTARATE-DEPENDENT OXYGENASE PROMOTER FROM MAIZE AND ITS USE

CROSS REFERENCE TO RELATED APPLICATIONS

This application claims the benefit of U.S. Provisional Application No. 60/636,890, filed on Dec. 17, 2004, which is herein incorporated by reference in its entirety.

FIELD OF THE INVENTION

The present invention relates to the field of plant molecular biology, more particularly to regulation of gene expression in plants.

BACKGROUND OF THE INVENTION

Recent advances in plant genetic engineering have enabled the engineering of plants having improved characteristics or traits, such as disease resistance, insect resistance, herbicide resistance, enhanced stability or shelf-life of the ultimate consumer product obtained from the plants and improvement of the nutritional quality of the edible portions of the plant. Thus, one or more desired genes from a source different than the plant, but engineered to impart different or improved characteristics or qualities, can be incorporated into the plant's genome. New gene(s) can then be expressed in the plant cell to exhibit the desired phenotype such as a new trait or characteristic.

The proper regulatory signals must be present and be in the proper location with respect to the gene in order to obtain expression of the newly inserted gene in the plant cell. These regulatory signals may include, but are not limited to, a promoter region, a 5' non-translated leader sequence and a 3' transcription termination/polyadenylation sequence.

A promoter is a DNA sequence that directs cellular machinery of a plant to produce RNA from the contiguous coding sequence downstream (3') of the promoter. The promoter region influences the rate, developmental stage, and cell type in which the RNA transcript of the gene is made. The RNA transcript is processed to produce messenger RNA (mRNA) which serves as a template for translation of the RNA sequence into the amino acid sequence of the encoded polypeptide. The 5' non-translated leader sequence is a region of the mRNA upstream of the protein coding region that may play a role in initiation and translation of the mRNA. The 3' transcription termination/polyadenylation signal is a non-translated region downstream of the protein coding region that functions in the plant cells to cause termination of the RNA transcript and the addition of polyadenylate nucleotides to the 3' end of the RNA.

Expression of heterologous DNA sequences in a plant host is dependent upon the presence of an operably linked promoter that is functional within the plant host. The type of promoter sequence chosen is based on when and where within the organism expression of the heterologous DNA is desired. Where expression in specific tissues or organs is desired, tissue-preferred promoters may be used. Where gene expression in response to a stimulus is desired, inducible promoters are the regulatory element of choice. In contrast, where continuous expression is desired throughout the cells of a plant, constitutive promoters are utilized.

An inducible promoter is a promoter that is capable of directly or indirectly activating transcription of one or more DNA sequences or genes in response to an inducer. In the absence of an inducer, the DNA sequences or genes will not be transcribed, or will be transcribed at a level lower than in an induced state. The inducer can be a chemical agent, such as a metabolite, growth regulator, herbicide or phenolic compound, or a physiological stress directly imposed upon the plant such as cold, drought, heat, salt, toxins. In the case of fighting plant pests, it is also desirable to have a promoter which is induced by plant pathogens, including plant insect pests, nematodes or disease agents such as a bacterium, virus or fungus. Contact with the pathogen will induce activation of transcription, such that a pathogen-fighting protein will be produced at a time when it will be effective in defending the plant. A pathogen-induced promoter may also be used to detect contact with a pathogen, for example by expression of a detectable marker, so that the need for application of pesticides can be assessed. A plant cell containing an inducible promoter may be exposed to an inducer by externally applying the inducer to the cell or plant such as by spraying, watering, heating, or by exposure to the operative pathogen.

A constitutive promoter is a promoter that directs expression of a gene throughout the various parts of a plant and continuously throughout plant development. Examples of some constitutive promoters that are widely used for inducing the expression of heterologous genes in transgenic plants include the nopaline synthase (NOS) gene promoter, from *Agrobacterium tumefaciens*, (U.S. Pat. No. 5,034,322), the cauliflower mosaic virus (CaMv) 35S and 19S promoters (U.S. Pat. No. 5,352,605), those derived from any of the several actin genes, which are known to be expressed in most cells types (U.S. Pat. No. 6,002,068), and the ubiquitin promoter, which is a gene product known to accumulate in many cell types.

Additional regulatory sequences upstream and/or downstream from the core promoter sequence may be included in expression constructs of transformation vectors to bring about varying levels of expression of heterologous nucleotide sequences in a transgenic plant. Genetically altering plants through the use of genetic engineering techniques to produce plants with useful traits thus requires the availability of a variety of promoters.

In order to maximize the commercial application of transgenic plant technology, it may be useful to direct the expression of the introduced DNA in a site-specific manner. For example, it may be useful to produce toxic defensive compounds in tissues subject to pathogen attack, but not in tissues that are to be harvested and eaten by consumers. By site-directing the synthesis or storage of desirable proteins or compounds, plants can be manipulated as factories, or production systems, for a tremendous variety of compounds with commercial utility. Cell-specific promoters provide the ability to direct the synthesis of compounds, spatially and temporally, to highly specialized tissues or organs, such as roots, leaves, vascular tissues, embryos, seeds, or flowers.

Alternatively, it may be useful to inhibit expression of a native DNA sequence within a plant's tissues to achieve a desired phenotype. Such inhibition might be accomplished with transformation of the plant to comprise a tissue-preferred promoter operably linked to an antisense nucleotide sequence, such that expression of the antisense sequence produces an RNA transcript that interferes with translation of the mRNA of the native DNA sequence.

Of particular interest are promoters that are induced by the feeding of insect pests. Insect pests are a major factor in the loss of the world's agricultural crops. Insect pest-related crop loss from corn rootworm alone has reached one billion dollars a year. The western corn rootworm (WCRW) is a major insect pest of corn or maize in many regions of the world. While not as important a pest as the western corn rootworm, the southern corn rootworm and northern corn rootworm may also cause significant economic damage to corn. Damage from corn rootworms may result in increased lodging, reduced drought tolerance and ultimately, crop yield reductions. Another one of the leading pests is *Ostrinia nubilalis*, commonly called the European corn borer (ECB).

Since the patterns of expression of a chimeric gene (or genes) introduced into a plant are controlled using promoters, there is an ongoing interest in the isolation and identification of novel promoters which are capable of controlling expression of a chimeric gene or (genes).

SUMMARY OF THE INVENTION

Compositions and methods for regulating gene expression in a plant are provided. Compositions comprise novel nucleotide sequences for an inducible promoter that initiates transcription in response to wounding or feeding by insect pests. More particularly, a transcriptional initiation region isolated from maize is provided. Further embodiments of the invention comprise the nucleotide sequence set forth in SEQ ID NO: 1, a fragment of the nucleotide sequence set forth in SEQ ID NO: 1, and the plant promoter sequences deposited with the American Type Culture Collection (ATCC) on Nov. 3, 2004 in a bacterial host as Patent Deposit No. PTA-6278. The embodiments of the invention further comprise nucleotide sequences having at least 95% sequence identity to the sequences set forth in SEQ ID NO: 1, and which drive wound- and insect-inducible expression of an operably linked nucleotide sequence. Also included are functional fragments of the sequence set forth as SEQ ID NO: 1 which drive wound- and insect-inducible expression of an operably linked nucleotide sequence.

Embodiments of the invention also include DNA constructs comprising a promoter operably linked to a heterologous nucleotide sequence of interest wherein said promoter is capable of driving expression of said nucleotide sequence in a plant cell and said promoter comprises the nucleotide sequences disclosed herein. Embodiments of the invention further provide expression vectors, and plants or plant cells having stably incorporated into their genomes a DNA construct mentioned above. Additionally, compositions include transgenic seed of such plants.

Method embodiments comprise a means for selectively expressing a nucleotide sequence in a plant, comprising transforming a plant cell with a DNA construct, and regenerating a transformed plant from said plant cell, said DNA construct comprising a promoter and a heterologous nucleotide sequence operably linked to said promoter, wherein said promoter initiates wound- and insect-inducible transcription of said nucleotide sequence in a plant cell. In this manner, the promoter sequences are useful for controlling the expression of operably linked coding sequences in an inducible manner.

Downstream from and under the transcriptional initiation regulation of the promoter will be a sequence of interest that will provide for modification of the phenotype of the plant. Such modification includes modulating the production of an endogenous product, as to amount, relative distribution, or the like, or production of an exogenous expression product to provide for a novel function or product in the plant. For example, a heterologous nucleotide sequence that encodes a gene product that confers herbicide, salt, cold, drought, pathogen or insect resistance is encompassed.

In a further embodiment, a method for modulating expression of a gene in a stably transformed plant is provided, comprising the steps of (a) transforming a plant cell with a DNA construct comprising the promoter of the embodiments operably linked to at least one nucleotide sequence; (b) growing the plant cell under plant growing conditions and (c) regenerating a stably transformed plant from the plant cell wherein expression of the nucleotide sequence alters the phenotype of the plant.

BRIEF DESCRIPTION OF THE DRAWINGS

FIG. 1 is a northern blot showing 2-oxoglutarate-dependent oxygenase expression in root tissue from V5 stage corn plants, both with and without western corn rootworm infestation. No expression was detected in leaves in either case. Repot refers to transplanting the plant into fresh soil. Root damage caused by this process does not induce peroxidase expression. Thus, this figure demonstrates the pattern of root expression and inducibility by CRW, as predicted by the Lynx MPSS data. Further detail on this blot is provided in Example 2.

FIG. 2 is a northern blot showing a time course of 2-oxoglutarate-dependent oxygenase expression in root tissue following wounding. No expression was detected in leaf tissue at any time point in the experiment. Thus, this figure demonstrates the pattern of root expression and inducibility by wounding, as predicted by the Lynx MPSS data. Further detail on this blot is provided in Example 2.

FIG. 3 shows the sequence of the maize 2-oxoglutarate-dependent oxygenase promoter sequence. The positions of the TATA box, the transcriptional start site (TSS) mapped by 5' RACE, and other motifs of interest in the promoter sequence are indicated. Further detail is provided in Example 4.

DETAILED DESCRIPTION OF THE INVENTION

The embodiments of the invention comprise novel nucleotide sequences for plant promoters, particularly a wound and insect-inducible promoter for a maize 2-oxoglutarate-dependent oxygenase gene (hereinafter 2OD oxygenase gene), more particularly, the 2-oxoglutarate-dependent oxygenase gene promoter, hereinafter referred to as the 2OD oxygenase promoter. In particular, the embodiments provide for isolated nucleic acid molecules comprising the nucleotide sequence set forth in SEQ ID NO: 1, and the plant promoter sequence deposited in a bacterial host as Patent Deposit No. PTA-6278, on Nov. 3, 2004, and fragments, variants, and complements thereof.

Plasmids containing the plant promoter nucleotide sequences of the embodiments were deposited on Nov. 3, 2004 with the Patent Depository of the American Type Culture Collection (ATCC), at 10801 University Blvd., Manassas, Va. 20110-2209, and assigned Patent Deposit No. PTA-6278. This deposit will be maintained under the terms of the Budapest Treaty on the International Recognition of the Deposit of Microorganisms for the Purposes of Patent Procedure. This deposit was made merely as a convenience for those of skill in the art and is not an admission that a deposit is required under 35 USC §112. The deposit will irrevocably and without restriction or condition be available to the public upon issuance of a patent. However, it should be understood that the availability of a deposit does not constitute a license to practice the subject invention in derogation of patent rights granted by government action.

The promoter sequences of the embodiments are useful for expressing operably linked nucleotide sequences in an inducible manner, particularly in an insect-pest feeding or wound-inducible manner. The sequences also find use in the construction of expression vectors for subsequent transformation into plants of interest, as probes for the isolation of other 2OD oxygenase gene promoters, as molecular markers, and the like.

The maize 2OD oxygenase promoter of the embodiments was isolated from maize genomic DNA. The specific method used to obtain the 2OD oxygenase promoter of the present invention is described in Example 4 in the experimental section of this application.

The embodiments encompass isolated or substantially purified nucleic acid compositions. An "isolated" or "purified" nucleic acid molecule, or biologically active portion thereof, is substantially free of other cellular material, or culture medium when produced by recombinant techniques, or substantially free of chemical precursors or other chemicals when chemically synthesized. An "isolated" nucleic acid is substantially free of sequences (including protein encoding sequences) that naturally flank the nucleic acid (i.e., sequences located at the 5' and 3' ends of the nucleic acid) in the genomic DNA of the organism from which the nucleic acid is derived. For example, in various embodiments, the isolated nucleic acid molecule can contain less than about 5 kb, 4 kb, 3 kb, 2 kb, 1 kb, 0.5 kb, or 0.1 kb of nucleotide sequences that naturally flank the nucleic acid molecule in genomic DNA of the cell from which the nucleic acid is derived.

This maize 2OD oxygenase gene is preferentially expressed in maize root tissue in response to damage elicited by corn root worm feeding or mechanical damage as indicated by Lynx Massively Parallel Signature Sequencing (MPSS) and further discussed in Example 1. 2OD oxygenases are involved in oxidation reactions using oxygen and are found in the biosynthetic pathways of many primary and secondary metabolites. Another closely related 2OD oxygenase gene displaying 81% amino acid identity to the above predicted gene product is implicated in DIMBOA biosynthesis. DIMBOA, a benzoxazinoid, is a natural pesticide and serves as an important factor of host plant resistance against microbial diseases and insects and as allelochemicals.

The 2OD oxygenase promoter sequence directs expression of operably linked nucleotide sequences in an inducible manner. Therefore, 2OD oxygenase promoter sequences find use in the inducible expression of an operably linked nucleotide sequence of interest. Particularly, the promoter of the embodiments acts to induce expression following wounding or the feeding activity of an insect pest.

The compositions of the embodiments include isolated nucleic acid molecules comprising the promoter nucleotide sequence set forth in SEQ ID NO: 1. The term "promoter" is intended to mean a regulatory region of DNA usually comprising a TATA box capable of directing RNA polymerase II to initiate RNA synthesis at the appropriate transcription initiation site for a particular coding sequence. A promoter may additionally comprise other recognition sequences generally positioned upstream or 5' to the TATA box, referred to as upstream promoter elements, which influence the transcription initiation rate. It is recognized that having identified the nucleotide sequences for the promoter regions disclosed herein, it is within the state of the art to isolate and identify further regulatory elements in the 5' untranslated region upstream from the particular promoter regions identified herein. Thus, for example, the promoter regions disclosed herein may further comprise upstream regulatory elements such as those responsible for tissue and temporal expression of the coding sequence, enhancers, and the like. See particularly Australian Patent No. AU-A-77751/94 and U.S. Pat. Nos. 5,466,785 and 5,635,618. In the same manner, the promoter elements that enable inducible expression can be identified, isolated, and used with other core promoters to confer inducible expression. In this aspect of the embodiments, a "core promoter" is intended to mean a promoter without promoter elements.

In the context of this disclosure, the term "regulatory element" also refers to a sequence of DNA, usually, but not always, upstream (5') to the coding sequence of a structural gene, which includes sequences which control the expression of the coding region by providing the recognition for RNA polymerase and/or other factors required for transcription to start at a particular site. An example of a regulatory element that provides for the recognition for RNA polymerase or other transcriptional factors to ensure initiation at a particular site is a promoter element. A promoter element comprises a core promoter element, responsible for the initiation of transcription, as well as other regulatory elements (as discussed elsewhere in this application) that modify gene expression. It is to be understood that nucleotide sequences, located within introns, or 3' of the coding region sequence may also contribute to the regulation of expression of a coding region of interest. Examples of suitable introns include, but are not limited to, the maize IVS6 intron, or the maize actin intron. A regulatory element may also include those elements located downstream (3') to the site of transcription initiation, or within transcribed regions, or both. In the context of the present disclosure, a post-transcriptional regulatory element may include elements that are active following transcription initiation, for example translational and transcriptional enhancers, translational and transcriptional repressors, and mRNA stability determinants.

The regulatory elements, or fragments thereof, of the embodiments may be operatively associated with heterologous regulatory elements or promoters in order to modulate the activity of the heterologous regulatory element. Such modulation includes enhancing or repressing transcriptional activity of the heterologous regulatory element, modulating post-transcriptional events, or both enhancing or repressing transcriptional activity of the heterologous regulatory element and modulating post-transcriptional events. For example, one or more regulatory elements, or fragments thereof, of the embodiments may be operatively associated with constitutive, inducible, or tissue specific promoters or fragment thereof, to modulate the activity of such promoters within desired tissues within plant cells.

The maize 2OD oxygenase promoter sequence, when assembled within a DNA construct such that the promoter is operably linked to a nucleotide sequence of interest, enables expression of the nucleotide sequence in the cells of a plant stably transformed with this DNA construct. The term "operably linked" is intended to mean that the transcription or translation of the heterologous nucleotide sequence is under the influence of the promoter sequence. "Operably linked" is also intended to mean the joining of two nucleotide sequences such that the coding sequence of each DNA fragment remains in the proper reading frame. In this manner, the nucleotide sequences for the promoters of the embodiments are provided in DNA constructs along with the nucleotide sequence of interest, typically a heterologous nucleotide sequence, for expression in the plant of interest.

The term "heterologous nucleotide sequence" is intended to mean a sequence that is not naturally operably linked with the promoter sequence. While this nucleotide sequence is heterologous to the promoter sequence, it may be homologous, or native; or heterologous, or foreign, to the plant host.

It is recognized that the promoters of the embodiments may be used with their native coding sequences to increase or decrease expression, thereby resulting in a change in phenotype of the transformed plant.

Modifications of the isolated promoter sequences of the embodiments can provide for a range of expression of the heterologous nucleotide sequence. Thus, they may be modified to be weak promoters or strong promoters. Generally, a "weak promoter" is intended to mean a promoter that drives expression of a coding sequence at a low level. A "low level" of expression is intended to mean expression at levels of about 1/10,000 transcripts to about 1/100,000 transcripts to about 1/500,000 transcripts. Conversely, a strong promoter drives expression of a coding sequence at a high level, or at about 1/10 transcripts to about 1/100 transcripts to about 1/1,000 transcripts.

Fragments and variants of the disclosed promoter sequences are also encompassed by the embodiments. A "fragment" is intended to mean a portion of the promoter sequence. Fragments of a promoter sequence may retain biological activity and hence encompass fragments capable of driving inducible expression of an operably linked nucleotide sequence. Thus, for example, less than the entire promoter sequence disclosed herein may be utilized to drive expression of an operably linked nucleotide sequence of interest, such as a nucleotide sequence encoding a heterologous protein. Those skilled in the art are able to determine whether such fragments decrease expression levels or alter the nature of expression, i.e., constitutive or inducible expression. Alternatively, fragments of a promoter nucleotide sequence that are useful as hybridization probes, such as described below, may not retain this regulatory activity. Thus, fragments of a nucleotide sequence may range from at least about 20 nucleotides, about 50 nucleotides, about 100 nucleotides, and up to the full-length nucleotide sequences of the embodiments.

Thus, a fragment of a 2OD oxygenase promoter nucleotide sequence may encode a biologically active portion of the 2OD oxygenase promoter or it may be a fragment that can be used as a hybridization probe or PCR primer using methods disclosed below. A biologically active portion of a 2OD oxygenase promoter can be prepared by isolating a portion of the 2OD oxygenase promoter nucleotide sequence and assessing the activity of that portion of the 2OD oxygenase promoter. Nucleic acid molecules that are fragments of a promoter nucleotide sequence comprise at least 15, 20, 25, 30, 35, 40, 45, 50, 75, 100, 325, 350, 375, 400, 425, 450, 500, 550, 600, 650, 700, 800, 900, 1000 or up to the number of nucleotides present in the full-length promoter nucleotide sequence disclosed herein, e.g. 1116 nucleotides for SEQ ID NO: 1.

The nucleotides of such fragments will usually comprise the TATA recognition sequence of the particular promoter sequence. Such fragments may be obtained by use of restriction enzymes to cleave the naturally occurring promoter nucleotide sequence disclosed herein; by synthesizing a nucleotide sequence from the naturally occurring sequence of the promoter DNA sequence; or may be obtained through the use of PCR technology. See particularly, Mullis et al. (1987) *Methods Enzymol* 155:335–350, and Erlich, ed. (1989) *PCR Technology* (Stockton Press, New York). Variants of these promoter fragments, such as those resulting from site-directed mutagenesis and procedures such as DNA "shuffling," are also encompassed by the compositions of the embodiments.

An "analogue" of the regulatory elements of the embodiments includes any substitution, deletion, or addition to the sequence of a regulatory element provided that said analogue maintains at least one regulatory property associated with the activity of the regulatory element of the embodiments. Such properties include directing organ specificity, tissue specificity, or a combination thereof, or temporal activity, or developmental activity, or a combination thereof.

The term "variants" is intended to mean sequences having substantial similarity with a promoter sequence disclosed herein. For nucleotide sequences, naturally occurring variants such as these can be identified with the use of well-known molecular biology techniques, as, for example, with polymerase chain reaction (PCR) and hybridization techniques as outlined below. Variant nucleotide sequences also include synthetically derived nucleotide sequences, such as those generated, for example, by using site-directed mutagenesis. Generally, variants of a particular nucleotide sequence of the embodiments will have at least 40%, 50%, 60%, 65%, 70%, 75%, 80%, 85%, 90%, 91%, 92%, 93%, 94%, to 95%, 96%, 97%, 98%, 99% or more sequence identity to that particular nucleotide sequence as determined by sequence alignment programs described elsewhere herein using default parameters. Biologically active variants are also encompassed by the embodiments. Biologically active variants include, for example, the native promoter sequences of the embodiments having one or more nucleotide substitutions, deletions, or insertions. Promoter activity may be measured by using techniques such as northern blot analysis, reporter activity measurements taken from transcriptional fusions, and the like. See, for example, Sambrook et al. (1989) *Molecular Cloning: A Laboratory Manual* (2d ed., Cold Spring Harbor Laboratory Press, Cold Spring Harbor, N.Y.), hereinafter "Sambrook," herein incorporated by reference. Alternatively, levels of a reporter gene such as green fluorescent protein (GFP) or the like produced under the control of a promoter fragment or variant can be measured. See, for example, U.S. Pat. No. 6,072,050, herein incorporated by reference.

Methods for mutagenesis and nucleotide sequence alterations are well known in the art. See, for example, Kunkel (1985) *Proc. Natl. Acad. Sci. USA* 82:488–492; Kunkel et al. (1987) *Methods in Enzymol.* 154:367–382; U.S. Pat. No. 4,873,192; Walker and Gaastra, eds. (1983) *Techniques in Molecular Biology* (MacMillan Publishing Company, New York) and the references cited therein.

Variant promoter nucleotide sequences also encompass sequences derived from a mutagenic and recombinogenic procedure such as DNA shuffling. With such a procedure, one or more different promoter sequences can be manipulated to create a new promoter possessing the desired properties. In this manner, libraries of recombinant polynucleotides are generated from a population of related sequence polynucleotides comprising sequence regions that have substantial sequence identity and can be homologously recombined in vitro or in vivo. Strategies for such DNA shuffling are known in the art. See, for example, Stemmer (1994) *Proc. Natl. Acad. Sci. USA* 91:10747–10751; Stemmer (1994) *Nature* 370:389–391; Crameri et al. (1997) *Nature Biotech.* 15:436–438; Moore et al. (1997) *J. Mol. Biol.* 272:336–347; Zhang et al. (1997) *Proc. Natl. Acad. Sci. USA* 94:4504–4509; Crameri et al. (1998) *Nature* 391: 288–291; and U.S. Pat. Nos. 5,605,793 and 5,837,458.

The nucleotide sequences of the embodiments can be used to isolate corresponding sequences from other organisms, such as other plants, for example, other monocots. In this manner, methods such as PCR, hybridization, and the like can be used to identify such sequences based on their sequence homology to the sequence set forth herein. Sequences isolated based on their sequence identity to the entire 2OD oxygenase promoter sequence set forth herein or to fragments thereof are encompassed by the embodiments. The promoter regions of the embodiments may be isolated from any plant, including, but not limited to corn (*Zea mays*), *Brassica* (*Brassica napus, Brassica rapa* ssp.), alfalfa (*Medicago sativa*), rice (*Oryza sativa*), rye (*Secale cereale*), sorghum (*Sorghum bicolor, Sorghum vulgare*), sunflower (*Helianthus annuus*), wheat (*Triticum aestivum*), soybean (*Glycine max*), tobacco (*Nicotiana tabacum*), potato (*Solanum tuberosum*), peanuts (*Arachis hypogaea*), cotton (*Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), oats, barley, safflower, vegetables, ornamentals, and conifers.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, supra. See also Innis et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers, and the like.

In hybridization techniques, all or part of a known nucleotide sequence is used as a probe that selectively hybridizes to other corresponding nucleotide sequences present in a population of cloned genomic DNA fragments or cDNA fragments (i.e., genomic or cDNA libraries) from a chosen organism. The hybridization probes may be genomic DNA fragments, cDNA fragments, RNA fragments, or other oligonucleotides, and may be labeled with a detectable group such as $^{32}P$, or any other detectable marker. Thus, for example, probes for hybridization can be made by labeling synthetic oligonucleotides based on the 2OD oxygenase promoter sequence. Methods for preparation of probes for hybridization and for construction of cDNA and genomic libraries are generally known in the art and are disclosed in Sambrook, supra.

For example, the entire 2OD oxygenase promoter sequence disclosed herein, or one or more portions thereof, may be used as a probe capable of specifically hybridizing to corresponding 2OD oxygenase promoter sequences. To achieve specific hybridization under a variety of conditions, such probes include sequences that are unique among 2OD oxygenase promoter sequences and are generally at least about 10 nucleotides in length, including sequences of at least about 20 nucleotides in length. Such probes may be used to amplify corresponding 2OD oxygenase promoter sequences from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook supra).

Hybridization of such sequences may be carried out under stringent conditions. "Stringent conditions" or "stringent hybridization conditions" are conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, including those less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. for at least 30 minutes. Duration of hybridization is generally less than about 24 hours, usually about 4 to about 12 hours.

Specificity is typically the function of post-hybridization washes, the critical factors being the ionic strength and temperature of the final wash solution. For DNA-DNA hybrids, the thermal melting point ($T_m$) can be approximated from the equation of Meinkoth and Wahl (1984) *Anal. Biochem.* 138:267–284: $T_m$=81.5° C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≧90% identity are sought, the $T_m$ can be decreased 10° C. Generally, stringent conditions are selected to be about 5° C. lower than the $T_m$ for the specific sequence and its complement at a defined ionic strength and pH. However, severely stringent conditions can utilize a hybridization and/or wash at 1, 2, 3, or 4° C. lower than the $T_m$; moderately stringent conditions can utilize a hybridization and/or wash at 6, 7, 8, 9, or 10° C. lower than the $T_m$; low stringency conditions can utilize a hybridization and/or wash at 11, 12, 13, 14,15, or 20° C. lower than the $T_m$. Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is preferred to increase the SSC concentration so that a higher temperature can be used. An extensive guide to the hybridization of nucleic acids is found in Tijssen (1993) *Laboratory Techniques in Biochemistry and Molecular Biology—Hybridization with Nucleic Acid Probes*, Part I, Chapter 2 (Elsevier, New York); and Ausubel et al., eds. (1995) *Current Protocols in Molecular Biology*, Chapter 2 (Greene Publishing and Wiley-Interscience, New York), hereinafter "Ausubel". See also Sambrook supra.

Thus, isolated sequences that have inducible promoter activity and which hybridize under stringent conditions to the 2OD oxygenase promoter sequences disclosed herein, or to fragments thereof, are encompassed by the embodiments.

In general, sequences that have promoter activity and hybridize to the promoter sequences disclosed herein will be at least 40% to 50% homologous, about 60%, 70%, 80%, 85%, 90%, 95% to 98% homologous or more with the disclosed sequences. That is, the sequence similarity of sequences may range, sharing at least about 40% to 50%, about 60% to 70%, and about 80%, 85%, 90%, 95% to 98% sequence similarity.

The following terms are used to describe the sequence relationships between two or more nucleic acids or polynucleotides: (a) "reference sequence", (b) "comparison window", (c) "sequence identity", (d) "percentage of sequence identity", and (e) "substantial identity".

(a) As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be 30, 40, 50, 100, or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Preferred, non-limiting examples of such mathematical algorithms are the algorithm of Myers and Miller (1988) *CABIOS* 4:11–17; the local homology algorithm of Smith et al. (1981) *Adv. Appl. Math.* 2:482; the homology alignment algorithm of Needleman and Wunsch (1970) *J. Mol. Biol.* 48:443–453; the algorithm of Pearson and Lipman (1988) *Proc. Natl. Acad. Sci.* 85:2444–2448; the algorithm of Karlin and Altschul (1990) *Proc. Natl. Acad. Sci. USA* 87:2264, modified as in Karlin and Altschul (1993) *Proc. Natl. Acad. Sci. USA* 90:5873–5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0); the ALIGN PLUS program (Version 3.0, copyright 1997): and GAP, BESTFIT, BLAST, FASTA, and TFASTA in the Wisconsin Genetics Software Package of Genetics Computer Group, Version 10 (available from Accelrys, 9685 Scranton Road, San Diego, Calif., 92121, USA). The scoring matrix used in Version 10 of the Wisconsin Genetics Software Package is BLOSUM62 (see Henikoff and Henikoff (1989) *Proc. Natl. Acad. Sci. USA* 89:10915).

Alignments using these programs can be performed using the default parameters. The CLUSTAL program is well described by Higgins et al. (1988) *Gene* 73:237–244 (1988); Higgins et al. (1989) *CABIOS* 5:151–153; Corpet et al. (1988) *Nucleic Acids Res.* 16:10881–90; Huang et al. (1992) *CABIOS* 8:155–65; and Pearson et al. (1994) *Meth. Mol. Biol.* 24:307–331. The ALIGN and the ALIGN PLUS programs are based on the algorithm of Myers and Miller (1988) supra. A PAM120 weight residue table, a gap length penalty of 12, and a gap penalty of 4 can be used with the ALIGN program when comparing amino acid sequences. The BLAST programs of Altschul et al (1990) *J. Mol. Biol.* 215:403 are based on the algorithm of Karlin and Altschul (1990) supra. BLAST nucleotide searches can be performed with the BLASTN program, score=100, wordlength=12, to obtain nucleotide sequences homologous to a nucleotide sequence encoding a protein of the embodiments. BLAST protein searches can be performed with the BLASTX program, score=50, wordlength=3, to obtain amino acid sequences homologous to a protein or polypeptide of the embodiments. To obtain gapped alignments for comparison purposes, Gapped BLAST (in BLAST 2.0) can be utilized as described in Altschul et al. (1997) *Nucleic Acids Res.* 25:3389. Alternatively, PSI-BLAST (in BLAST 2.0) can be used to perform an iterated search that detects distant relationships between molecules. See Altschul et al. (1997) supra. When utilizing BLAST, Gapped BLAST, PSI-BLAST, the default parameters of the respective programs (e.g., BLASTN for nucleotide sequences, BLASTX for proteins) can be used. See the web site for the National Center for Biotechnology Information on the world wide web. Alignment may also be performed manually by inspection.

Unless otherwise stated, sequence identity/similarity values provided herein refer to the value obtained using the GAP program with default parameters, or any equivalent program. By "equivalent program" is intended any sequence comparison program that, for any two sequences in question, generates an alignment having identical nucleotide or amino acid residue matches and an identical percent sequence identity when compared to the corresponding alignment generated by GAP.

The GAP program uses the algorithm of Needleman and Wunsch (1970) supra, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the Wisconsin Genetics Software Package for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

(c) As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

(e)(i) The term "substantial identity" of polynucleotide sequences means that a polynucleotide comprises a sequence that has at least 70% sequence identity, at least 80%, at least 90%, or at least 95%, compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 60%, 70%, 80%, 90%, and at least 95%.

Another indication that nucleotide sequences are substantially identical is if two molecules hybridize to each other under stringent conditions. Generally, stringent conditions are selected to be about 5° C. lower than the $T_m$ for the specific sequence at a defined ionic strength and pH. However, stringent conditions encompass temperatures in the range of about 1° C. to about 20° C. lower than the $T_m$, depending upon the desired degree of stringency as otherwise qualified herein. Nucleic acids that do not hybridize to each other under stringent conditions are still substantially identical if the polypeptides they encode are substantially identical. This may occur, e.g., when a copy of a nucleic acid is created using the maximum codon degeneracy permitted by the genetic code. One indication that two nucleic acid sequences are substantially identical is when the polypeptide encoded by the first nucleic acid is immunologically cross reactive with the polypeptide encoded by the second nucleic acid.

The 2OD oxygenase promoter sequence disclosed herein, as well as variants and fragments thereof, are useful for genetic engineering of plants, e.g. for the production of a transformed or transgenic plant, to express a phenotype of interest. As used herein, the terms "transformed plant" and "transgenic plant" refer to a plant that comprises within its genome a heterologous polynucleotide. Generally, the heterologous polynucleotide is stably integrated within the genome of a transgenic or transformed plant such that the polynucleotide is passed on to successive generations. The heterologous polynucleotide may be integrated into the genome alone or as part of a recombinant DNA construct. It is to be understood that as used herein the term "transgenic" includes any cell, cell line, callus, tissue, plant part, or plant the genotype of which has been altered by the presence of heterologous nucleic acid including those transgenics initially so altered as well as those created by sexual crosses or asexual propagation from the initial transgenic. The term "transgenic" as used herein does not encompass the alteration of the genome (chromosomal or extra-chromosomal) by conventional plant breeding methods or by naturally occurring events such as random cross-fertilization, non-recombinant viral infection, non-recombinant bacterial transformation, non-recombinant transposition, or spontaneous mutation.

A transgenic "event" is produced by transformation of plant cells with a heterologous DNA construct, including a nucleic acid expression cassette that comprises a transgene of interest, the regeneration of a population of plants resulting from the insertion of the transgene into the genome of the plant, and selection of a particular plant characterized by insertion into a particular genome location. An event is characterized phenotypically by the expression of the transgene. At the genetic level, an event is part of the genetic makeup of a plant. The term "event" also refers to progeny produced by a sexual outcross between the transformant and another variety that include the heterologous DNA.

As used herein, the term "plant" includes reference to whole plants, plant organs (e.g., leaves, stems, roots, etc.), seeds, plant cells, and progeny of same. Parts of transgenic plants are to be understood within the scope of the embodiments to comprise, for example, plant cells, protoplasts, tissues, callus, embryos as well as flowers, stems, fruits, ovules, leaves, or roots originating in transgenic plants or their progeny previously transformed with a DNA molecule of the embodiments, and therefore consisting at least in part of transgenic cells.

As used herein, the term "plant cell" includes, without limitation, seeds suspension cultures, embryos, meristematic regions, callus tissue, leaves, roots, shoots, gametophytes, sporophytes, pollen, and microspores. The class of plants that can be used in the methods disclosed herein is generally as broad as the class of higher plants amenable to transformation techniques, including both monocotyledonous and dicotyledonous plants.

The promoter sequences and methods disclosed herein are useful in regulating expression of any heterologous nucleotide sequence in a host plant. Thus, the heterologous nucleotide sequence operably linked to the promoters disclosed herein may be a structural gene encoding a protein of interest. Genes of interest are reflective of the commercial markets and interests of those involved in the development of the crop. Crops and markets of interest change, and as developing nations open up world markets, new crops and technologies will emerge also. In addition, as our understanding of agronomic traits and characteristics such as yield and heterosis increase, the choice of genes for transformation will change accordingly. General categories of genes of interest for the embodiments include, for example, those genes involved in information, such as zinc fingers, those involved in communication, such as kinases, and those involved in housekeeping, such as heat shock proteins. More specific categories of transgenes, for example, include genes encoding proteins conferring resistance to abiotic stress, such as drought, temperature, salinity, and toxins such as pesticides and herbicides, or to biotic stress, such as attacks by fungi, viruses, bacteria, insects, and nematodes, and development of diseases associated with these organisms. Various changes in phenotype are of interest including modifying expression of a gene in a plant, altering a plant's pathogen or insect defense mechanism, increasing the plant's tolerance to herbicides, altering plant development to respond to environmental stress, and the like. The results can be achieved by providing expression of heterologous or increased expression of endogenous products in plants. Alternatively, the results can be achieved by providing for a reduction of expression of one or more endogenous products, particularly enzymes, transporters, or cofactors, or affecting nutrients uptake in the plant. These changes result in a change in phenotype of the transformed plant.

It is recognized that any gene of interest can be operably linked to the promoter sequences of the embodiments and expressed in a plant.

A DNA construct comprising one of these genes of interest can be used with transformation techniques, such as those described below, to create disease or insect resistance in susceptible plant phenotypes or to enhance disease or insect resistance in resistant plant phenotypes. Accordingly, the embodiments encompass methods that are directed to protecting plants against fungal pathogens, bacteria, viruses, nematodes, insects, and the like. By "disease resistance" or "insect resistance" is intended that the plants avoid the harmful symptoms that are the outcome of the plant-pathogen interactions.

Disease resistance and insect resistance genes such as lysozymes, cecropins, maganins, or thionins for antibacterial protection, or the pathogenesis-related (PR) proteins such as glucanases and chitinases for anti-fungal protection, or Bacillus thuringiensis endotoxins, protease inhibitors, collagenases, lectins, and glycosidases for controlling nematodes or insects are all examples of useful gene products.

Pathogens of the embodiments include, but are not limited to, viruses or viroids, bacteria, insects, nematodes, fungi, and the like. Viruses include tobacco or cucumber mosaic virus, ringspot virus, necrosis virus, maize dwarf mosaic virus, etc. Nematodes include parasitic nematodes such as root knot, cyst, and lesion nematodes, etc.

Insect resistance genes may encode resistance to pests that have great yield drag such as rootworm, cutworm, European corn borer, and the like. Such genes include, for example, Bacillus thuringiensis toxic protein genes (U.S. Pat. Nos. 5,366,892; 5,747,450; 5,737,514; 5,723,756; 5,593,881; and Geiser et al. (1986) Gene 48:109); lectins (Van Damme et al. (1994) Plant Mol. Biol. 24:825); and the like.

Genes encoding disease resistance traits include detoxification genes, such as against fumonisin (U.S. Pat. No. 5,792,931) avirulence (avr) and disease resistance (R) genes (Jones et al. (1994) Science 266:789; Martin et al. (1993) Science 262:1432; Mindrinos et al. (1994) Cell 78:1089); and the like.

Herbicide resistance traits may be introduced into plants by genes coding for resistance to herbicides that act to inhibit the action of acetolactate synthase (ALS), in particular the sulfonylurea-type herbicides (e.g., the acetolactate synthase (ALS) gene containing mutations leading to such resistance, in particular the S4 and/or Hra mutations), genes coding for resistance to herbicides that act to inhibit action of glutamine synthase, such as phosphinothricin or basta (e.g., the bar gene), or other such genes known in the art. The bar gene encodes resistance to the herbicide basta, the nptII gene encodes resistance to the antibiotics kanamycin and geneticin, and the ALS gene encodes resistance to the herbicide chlorsulfuron.

Glyphosate resistance is imparted by mutant 5-enol pyruvylshikimate-3-phosphate synthase (EPSPS) and aroA genes. See, for example, U.S. Pat. No. 4,940,835 to Shah et al., which discloses the nucleotide sequence of a form of EPSPS which can confer glyphosate resistance. U.S. Pat. No. 5,627,061 to Barry et al. also describes genes encoding EPSPS enzymes. See also U.S. Pat. Nos. 6,248,876; 6,040,497; 5,804,425; 5,633,435; 5,145,783; 4,971,908; 5,312,910; 5,188,642; 4,940,835; 5,866,775; 6,225,114; 6,130,366; 5,310,667; 4,535,060; 4,769,061; 5,633,448; 5,510,471; RE 36,449; RE 37,287; and 5,491,288; and international publications WO 97/04103; WO 97/04114; WO 00/66746; WO 01/66704; WO 00/66747 and WO 00/66748, which are incorporated herein by reference for this purpose. Glyphosate resistance is also imparted to plants that express a gene that encodes a glyphosate oxido-reductase enzyme as described more fully in U.S. Pat. Nos. 5,776,760 and 5,463,175, which are incorporated herein by reference for this purpose. In addition glyphosate resistance can be imparted to plants by the over-expression of genes encoding glyphosate N-acetyltransferase. See, for example, U.S. patent application Ser. Nos. 10/004,357; 10/427,692, and 10/835,615.

Sterility genes can also be encoded in a DNA construct and provide an alternative to physical detasseling. Examples of genes used in such ways include male tissue-preferred genes and genes with male sterility phenotypes such as QM, described in U.S. Pat. No. 5,583,210. Other genes include kinases and those encoding compounds toxic to either male or female gametophytic development.

Commercial traits can also be encoded on a gene or genes that could increase for example, starch for ethanol production, or provide expression of proteins. Another important commercial use of transformed plants is the production of polymers and bioplastics such as described in U.S. Pat. No. 5,602,321. Genes such as β-Ketothiolase, PHBase (polyhydroxybutyrate synthase), and acetoacetyl-CoA reductase (see Schubert et al. (1988) J. Bacteriol. 170:5837–5847) facilitate expression of polyhydroxyalkanoates (PHAs).

Agronomically important traits that affect quality of grain, such as levels and types of oils, saturated and unsaturated, quality and quantity of essential amino acids, levels of cellulose, starch, and protein content can be genetically altered using the methods of the embodiments. Modifications include increasing content of oleic acid, saturated and unsaturated oils, increasing levels of lysine and sulfur, providing essential amino acids, and modifying starch. Hordothionin protein modifications in corn are described in U.S. Pat. Nos. 5,990,389; 5,885,801; 5,885,802 and 5,703,049; herein incorporated by reference. Another example is lysine and/or sulfur rich seed protein encoded by the soybean 2S albumin described in U.S. Pat. No. 5,850,016, filed Mar. 20, 1996, and the chymotrypsin inhibitor from barley, Williamson et al. (1987) Eur. J. Biochem. 165:99–106, the disclosures of which are herein incorporated by reference.

Exogenous products include plant enzymes and products as well as those from other sources including prokaryotes and other eukaryotes. Such products include enzymes, cofactors, hormones, and the like.

Examples of other applicable genes and their associated phenotype include the gene that encodes viral coat protein and/or RNA, or other viral or plant genes that confer viral resistance; genes that confer fungal resistance; genes that confer insect resistance; genes that promote yield improvement; and genes that provide for resistance to stress, such as dehydration resulting from heat and salinity, toxic metal or trace elements, or the like.

In other embodiments of the present invention, the 2OD oxygenase promoter sequences are operably linked to genes of interest that improve plant growth or increase crop yields under high plant density conditions. For example, the 2OD oxygenase promoter may be operably linked to nucleotide sequences expressing agronomically important genes that result in improved primary or lateral root systems. Such genes include, but are not limited to, nutrient/water transporters and growth inducers. Examples of such genes, include but are not limited to, maize plasma membrane $H^+$-ATPase (MHA2) (Frias et al. (1996) Plant Cell 8:1533–44); AKT1, a component of the potassium uptake apparatus in Arabidopsis (Spalding et al. (1999) J. Gen. Physiol. 113:909–18); RML genes, which activate cell division cycle in the root apical cells (Cheng et al. (1995) Plant Physiol. 108:881); maize glutamine synthetase genes (Sukanya et al. (1994) Plant Mol. Biol. 26:1935–46); and hemoglobin (Duff et al. (1997) J. Biol. Chem. 27:16749–16752; Arredondo-Peter et al. (1997) Plant Physiol. 115:1259–1266; Arredondo-Peter et al. (1997) Plant Physiol. 114:493–500 and references cited therein). The 2OD oxygenase promoter may also be useful in expressing antisense nucleotide sequences of genes that negatively affect root development under high-planting density conditions.

The heterologous nucleotide sequence operably linked to the 2OD oxygenase promoter and its related biologically active fragments or variants disclosed herein may be an antisense sequence for a targeted gene. The terminology "antisense DNA nucleotide sequence" is intended to mean a sequence that is in inverse orientation to the 5'-to-3' normal orientation of that nucleotide sequence. When delivered into a plant cell, expression of the antisense DNA sequence prevents normal expression of the DNA nucleotide sequence for the targeted gene. The antisense nucleotide sequence encodes an RNA transcript that is complementary to and capable of hybridizing to the endogenous messenger RNA (mRNA) produced by transcription of the DNA nucleotide sequence for the targeted gene. In this case, production of the native protein encoded by the targeted gene is inhibited to achieve a desired phenotypic response. Modifications of the antisense sequences may be made as long as the sequences hybridize to and interfere with expression of the corresponding mRNA. In this manner, antisense constructions having 70%, 80%, 85% sequence identity to the corresponding antisense sequences may be used. Furthermore, portions of the antisense nucleotides may be used to disrupt the expression of the target gene. Generally, sequences of at least 50 nucleotides, 100 nucleotides, 200 nucleotides, or greater may be used. Thus, the promoter sequences disclosed herein may be operably linked to antisense DNA sequences to reduce or inhibit expression of a native protein in the plant.

In other embodiments of the present invention, the 2OD oxygenase promoter sequences are operably linked to genes of interest that improve plant growth or increase crop yields under high plant density conditions. For example, the 2OD oxygenase promoter may be operably linked to nucleotide sequences expressing agronomically important genes that result in improved primary or lateral root systems. Such genes include, but are not limited to, nutrient/water transporters and growth inducers. Examples of such genes, include but are not limited to, maize plasma membrane $H^+$-ATPase (MHA2) (Frias et al. (1996) Plant Cell 8:1533–44); AKT1, a component of the potassium uptake apparatus in Arabidopsis (Spalding et al. (1999) J. Gen. Physiol. 113:909–18); RML genes, which activate cell division cycle in the root apical cells (Cheng et al. (1995) Plant Physiol. 108:881); maize glutamine synthetase genes (Sukanya et al. (1994) Plant Mol. Biol. 26:1935–46); and hemoglobin (Duff et al. (1997) J. Biol. Chem. 27:16749–16752; Arredondo-Peter et al. (1997) Plant Physiol. 115:1259–1266; Arredondo-Peter et al. (1997) Plant Physiol. 114:493–500 and references cited therein). The 2OD oxygenase promoter may also be useful in expressing antisense nucleotide sequences of genes that negatively affect root development under high-planting density conditions.

"RNAi" refers to a series of related techniques to reduce the expression of genes (See for example U.S. Pat. No. 6,506,559). Older techniques referred to by other names are now thought to rely on the same mechanism, but are given different names in the literature. These include "antisense inhibition," the production of antisense RNA transcripts capable of suppressing the expression of the target protein, and "co-suppression" or "sense-suppression," which refer to the production of sense RNA transcripts capable of suppressing the expression of identical or substantially similar foreign or endogenous genes (U.S. Pat. No. 5,231,020, incorporated herein by reference). Such techniques rely on the use of constructs resulting in the accumulation of double stranded RNA with one strand complementary to the target gene to be silenced. The 2OD oxygenase promoter sequence of the embodiments, and its related biologically active fragments or variants disclosed herein, may be used to drive expression of constructs that will result in RNA interference including microRNAs and siRNAs.

In one embodiment of the invention, DNA constructs will comprise a transcriptional initiation region comprising one of the promoter nucleotide sequences disclosed herein, or variants or fragments thereof, operably linked to a heterologous nucleotide sequence whose expression is to be controlled by the inducible promoter of the embodiments. Such a DNA construct is provided with a plurality of restriction sites for insertion of the nucleotide sequence to be under the transcriptional regulation of the regulatory regions. The DNA construct may additionally contain selectable marker genes.

The DNA construct will include in the 5'-3' direction of transcription, a transcriptional initiation region (i.e., an inducible promoter of the embodiments), translational initiation region, a heterologous nucleotide sequence of interest, a translational termination region and, optionally, a transcriptional termination region functional in the host organism. The regulatory regions (i.e., promoters, transcriptional regulatory regions, and translational termination regions) and/or the polynucleotide of the embodiments may be native/analogous to the host cell or to each other. Alternatively, the regulatory regions and/or the polynucleotide of the embodiments may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived, or, if from the same/analogous species, one or both are substantially modified from their original form and/or genomic locus, or the promoter is not the native promoter for the operably linked polynucleotide.

The optionally included termination region may be native with the transcriptional initiation region, may be native with the operably linked polynucleotide of interest, may be native with the plant host, or may be derived from another source (i.e., foreign or heterologous) to the promoter, the polynucleotide of interest, the host, or any combination thereof. Convenient termination regions are available from the Ti-plasmid of *A. tumefaciens*, such as the octopine synthase and nopaline synthase termination regions. See also Guerineau et al. (1991) *Mol. Gen. Genet.* 262:141–144; Proudfoot (1991) *Cell* 64:671–674; Sanfacon et al. (1991) *Genes Dev.* 5:141–149; Mogen et al. (1990) *Plant Cell* 2:1261–1272; Munroe et al. (1990) *Gene* 91:151–158; Ballas et al. (1989) *Nucleic Acids Res.* 17:7891–7903; and Joshi et al. (1987) *Nucleic Acids Res.* 15:9627–9639. In particular embodiments, the potato protease inhibitor II gene (PinII) terminator is used. See, for example, Keil et al. (1986) *Nucl. Acids Res.* 14:5641–5650; and An et al. (1989) *Plant Cell* 1:115–122, herein incorporated by reference in their entirety.

The DNA construct comprising a promoter sequence of the embodiments operably linked to a heterologous nucleotide sequence may also contain at least one additional nucleotide sequence for a gene to be cotransformed into the organism. Alternatively, the additional sequence(s) can be provided on another DNA construct.

Where appropriate, the heterologous nucleotide sequence whose expression is to be under the control of the inducible promoter sequence of the embodiments and any additional nucleotide sequence(s) may be optimized for increased expression in the transformed plant. That is, these nucleotide sequences can be synthesized using plant preferred codons for improved expression. Methods are available in the art for synthesizing plant-preferred nucleotide sequences. See, for example, U.S. Pat. Nos. 5,380,831 and 5,436,391, and Murray et al. (1989) *Nucleic Acids Res.* 17:477–498, herein incorporated by reference.

Additional sequence modifications are known to enhance gene expression in a cellular host. These include elimination of sequences encoding spurious polyadenylation signals, exon-intron splice site signals, transposon-like repeats, and other such well-characterized sequences that may be deleterious to gene expression. The G-C content of the heterologous nucleotide sequence may be adjusted to levels average for a given cellular host, as calculated by reference to known genes expressed in the host cell. When possible, the sequence is modified to avoid predicted hairpin secondary mRNA structures.

The DNA constructs may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein et al. (1989) *Proc. Nat. Acad. Sci. USA* 86:6126–6130); potyvirus leaders, for example, TEV leader (Tobacco Etch Virus) (Allison et al. (1986) *Virology* 154:9–20); MDMV leader (Maize Dwarf Mosaic Virus); human immunoglobulin heavy-chain binding protein (BiP) (Macejak et al. (1991) *Nature* 353: 90–94); untranslated leader from the coat protein mRNA of alfalfa mosaic virus (AMV RNA 4) (Jobling et al. (1987) *Nature* 325:622–625); tobacco mosaic virus leader (TMV) (Gallie et al. (1989) *Molecular Biology of RNA*, pages 237–256); and maize chlorotic mottle virus leader (MCMV) (Lommel et al. (1991) *Virology* 81:382–385). See also Della-Cioppa et al. (1987) *Plant Physiology* 84:965–968. Other methods known to enhance translation and/or mRNA stability can also be utilized, for example, introns, such as the maize Ubiquitin intron (Christensen and Quail (1996) *Transgenic Res.* 5:213–218; Christensen et al. (1992) *Plant Mol Biol* 18:675–689) or the maize AdhI intron (Kyozuka et al. (1991) *Mol. Gen. Genet.* 228:4048; Kyozuka et al. (1990) *Maydica* 35:353–357), and the like.

The DNA constructs of the embodiments can also include further enhancers, either translation or transcription enhancers, as may be required. These enhancer regions are well known to persons skilled in the art, and can include the ATG initiation codon and adjacent sequences. The initiation codon must be in phase with the reading frame of the coding sequence to ensure translation of the entire sequence. The translation control signals and initiation codons can be from a variety of origins, both natural and synthetic. Translational initiation regions may be provided from the source of the transcriptional initiation region, or from the structural gene. The sequence can also be derived from the regulatory element selected to express the gene, and can be specifically modified so as to increase translation of the mRNA. It is recognized that to increase transcription levels enhancers may be utilized in combination with the promoter regions of the embodiments. Enhancers are known in the art and include the SV40 enhancer region, the 35S enhancer element, and the like.

In preparing the DNA construct, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites. Restriction sites may be added or removed, superfluous DNA may be removed, or other modifications of the like may be made to the sequences of the embodiments. For this purpose, in vitro mutagenesis, primer repair, restriction, annealing, re-substitutions, for example, transitions and transversions, may be involved.

Reporter genes or selectable marker genes may be included in the DNA constructs. Examples of suitable reporter genes known in the art can be found in, for example, Jefferson et al. (1991) in *Plant Molecular Biology Manual*, ed. Gelvin et al. (Kluwer Academic Publishers), pp. 1–33; DeWet et al. (1987) *Mol. Cell. Biol.* 7:725–737; Goff et al. (1990) *EMBO J.* 9:2517–2522; Kain et al. (1995) *BioTechniques* 19:650–655; and Chiu et al. (1996) *Current Biology* 6:325–330.

Selectable marker genes for selection of transformed cells or tissues can include genes that confer antibiotic resistance or resistance to herbicides. Examples of suitable selectable marker genes include, but are not limited to, genes encoding resistance to chloramphenicol (Herrera Estrella et al. (1983) *EMBO J.* 2:987–992); methotrexate (Herrera Estrella et al. (1983) *Nature* 303:209–213; Meijer et al. (1991) *Plant Mol. Biol.* 16:807–820); hygromycin (Waldron et al. (1985) *Plant Mol. Biol.* 5:103–108; Zhijian et al. (1995) *Plant Science* 108:219–227); streptomycin (Jones et al. (1987) *Mol. Gen. Genet.* 210:86–91); spectinomycin (Bretagne-Sagnard et al. (1996) *Transgenic Res.* 5:131–137); bleomycin (Hille et al. (1990) *Plant Mol. Biol.* 7:171–176); sulfonamide (Guerineau et al. (1990) *Plant Mol. Biol.* 15:127–136); bromoxynil (Stalker et al. (1988) *Science* 242:419–423); glyphosate (Shaw et al. (1986) *Science* 233:478–481); phosphinothricin (DeBlock et al. (1987) *EMBO J.* 6:2513–2518).

Other genes that could serve utility in the recovery of transgenic events but might not be required in the final product would include, but are not limited to, examples such as GUS (b-glucuronidase; Jefferson (1987) *Plant Mol. Biol. Rep.* 5:387), GFP (green florescence protein; Chalfie et al. (1994) *Science* 263:802), luciferase (Riggs et al. (1987) *Nucleic Acids Res.* 15(19):8115 and Luehrsen et al. (1992) *Methods Enzymol.* 216:397–414), and the maize genes encoding for anthocyanin production (Ludwig et al. (1990) *Science* 247:449).

The nucleic acid molecules of the embodiments are useful in methods directed to expressing a nucleotide sequence in a plant. This may be accomplished by transforming a plant cell of interest with a DNA construct comprising a promoter identified herein, operably linked to a heterologous nucleotide sequence, and regenerating a stably transformed plant from said plant cell. The methods of the embodiments are also directed to inducibly expressing a nucleotide sequence in a plant. Those methods comprise transforming a plant cell with a DNA construct comprising a promoter identified herein that initiates transcription in a plant cell in an inducible manner, operably linked to a heterologous nucleotide sequence, regenerating a transformed plant from said plant cell, and subjecting the plant to the required stimulus to induce expression.

The DNA construct comprising the particular promoter sequence of the embodiments operably linked to a nucleotide sequence of interest can be used to transform any plant. In this manner, genetically modified, i.e. transgenic or transformed, plants, plant cells, plant tissue, seed, root, and the like can be obtained.

Plant species suitable for the embodiments include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Cofea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum.

Conifers that may be employed in practicing the embodiments include, for example, pines such as loblolly pine (*Pinus taeda*), slash pine (*Pinus elliotii*), ponderosa pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments may be crop plants (for example, corn, alfalfa, sunflower, *Brassica*, soybean, cotton, safflower, peanut, sorghum, wheat, millet, tobacco, etc.). For example, this invention is suitable for any member of the monocot plant family including, but not limited to, maize, rice, barley, oats, wheat, sorghum, rye, sugarcane, pineapple, yams, onion, banana, coconut, and dates.

As used herein, "vector" refers to a DNA molecule such as a plasmid, cosmid, or bacterial phage for introducing a nucleotide construct, for example, a DNA construct, into a host cell. Cloning vectors typically contain one or a small number of restriction endonuclease recognition sites at which foreign DNA sequences can be inserted in a determinable fashion without loss of essential biological function of the vector, as well as a marker gene that is suitable for use in the identification and selection of cells transformed with the cloning vector. Marker genes typically include genes that provide tetracycline resistance, hygromycin resistance, or ampicillin resistance.

The methods of the embodiments involve introducing a nucleotide construct into a plant. As used herein "introducing" is intended to mean presenting to the plant the nucleotide construct in such a manner that the construct gains access to the interior of a cell of the plant. The methods of the embodiments do not depend on a particular method for introducing a nucleotide construct to a plant, only that the nucleotide construct gains access to the interior of at least one cell of the plant. Methods for introducing nucleotide constructs into plants are known in the art including, but not limited to, stable transformation methods, transient transformation methods, and virus-mediated methods.

A "stable transformation" is one in which the nucleotide construct introduced into a plant integrates into the genome of the plant and is capable of being inherited by progeny thereof. "Transient transformation" means that a nucleotide construct introduced into a plant does not integrate into the genome of the plant.

The nucleotide constructs of the embodiments may be introduced into plants by contacting plants with a virus or viral nucleic acids. Generally, such methods involve incorporating a nucleotide construct of the embodiments within a viral DNA or RNA molecule. Methods for introducing nucleotide constructs into plants and expressing a protein encoded therein, involving viral DNA or RNA molecules, are known in the art. See, for example, U.S. Pat. Nos. 5,889,191, 5,889,190, 5,866,785, 5,589,367, and 5,316,931; herein incorporated by reference.

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway et al. (1986) *Biotechniques* 4:320–334), electroporation (Riggs et al. (1986) *Proc. Natl. Acad. Sci. USA* 83:5602–5606, *Agrobacterium*-mediated transformation (U.S. Pat. Nos. 5,981,840 and 5,563,055), direct gene transfer (Paszkowski et al. (1984) *EMBO J.* 3:2717–2722), and ballistic particle acceleration (see, for example, U.S. Pat. Nos. 4,945,050; 5,879,918; 5,886,244; 5,932,782; Tomes et al. (1995) in *Plant Cell, Tissue, and Organ Culture: Fundamental Methods*, ed. Gamborg and Phillips (Springer-Verlag, Berlin); and McCabe et al. (1988) *Biotechnology* 6:923–926). Also see Weissinger et al. (1988) *Ann. Rev. Genet.* 22:421–477; Sanford et al. (1987) *Particulate Science and Technology* 5:27–37 (onion); Christou et al. (1988) *Plant Physiol.* 87:671–674 (soybean); McCabe et al. (1988) *Bio/Technology* 6:923–926 (soybean); Finer and McMullen (1991) *In Vitro Cell Dev. Biol.* 27P:175–182 (soybean); Singh et al. (1998) *Theor. Appl. Genet.* 96:319–324 (soybean); Datta et al. (1990) *Biotechnology* 8:736–740 (rice); Klein et al. (1988) *Proc. Natl. Acad. Sci. USA* 85:4305–4309 (maize); Klein et al. (1988) *Biotechnology* 6:559–563 (maize); U.S. Pat. Nos. 5,240,855; 5,322,783 and 5,324,646; Klein etal. (1988) *Plant Physiol.* 91:440–444 (maize); Fromm et al. (1990) *Biotechnology* 8:833–839 (maize); Hooykaas-Van Slogteren et al. (1984) *Nature* (London) 311:763–764; U.S. Pat. No. 5,736,369 (cereals); Bytebier et al. (1987) *Proc. Natl. Acad. Sci. USA* 84:5345–5349 (Liliaceae); De Wet et al. (1985) in *The Experimental Manipulation of Ovule Tissues*, ed. Chapman et al. (Longman, New York), pp. 197–209 (pollen); Kaeppler et al. (1990) *Plant Cell Reports* 9:415–418 and Kaeppler et al. (1992) *Theor. Appl. Genet.* 84:560–566 (whisker-mediated transformation); D'Halluin et al. (1992) *Plant Cell* 4:1495–1505 (electroporation); Li et al. (1993) *Plant Cell Reports* 12:250–255 and Christou and Ford (1995) *Annals of Botany* 75:407413 (rice); Osjoda et al. (1996) *Nature Biotechnology* 14:745–750 (maize via *Agrobacterium tumefaciens*); all of which are herein incorporated by reference.

The cells that have been transformed may be grown into plants in accordance with conventional ways. See, for example, McCormick et al. (1986) *Plant Cell Reports* 5:81–84. These plants may then be grown, and either pollinated with the same transformed strain or different strains, and the resulting hybrid having inducible expression of the desired phenotypic characteristic identified. Two or more generations may be grown to ensure that inducible expression of the desired phenotypic characteristic is stably maintained and inherited and then seeds harvested to ensure inducible expression of the desired phenotypic characteristic has been achieved. Thus as used herein, "transformed seeds" refers to seeds that contain the nucleotide construct stably integrated into the plant genome.

There are a variety of methods for the regeneration of plants from plant tissue. The particular method of regeneration will depend on the starting plant tissue and the particular plant species to be regenerated. The regeneration, development and cultivation of plants from single plant protoplast transformants or from various transformed explants is well known in the art (Weissbach and Weissbach, (1988) In.: *Methods for Plant Molecular Biology*, (Eds.), Academic Press, Inc., San Diego, Calif.). This regeneration and growth process typically includes the steps of selection of transformed cells, culturing those individualized cells through the usual stages of embryonic development through the rooted plantlet stage. Transgenic embryos and seeds are similarly regenerated. The resulting transgenic rooted shoots are thereafter planted in an appropriate plant growth medium such as soil. Preferably, the regenerated plants are self-pollinated to provide homozygous transgenic plants. Otherwise, pollen obtained from the regenerated plants is crossed to seed-grown plants of agronomically important lines. Conversely, pollen from plants of these important lines is used to pollinate regenerated plants. A transgenic plant of the embodiments containing a desired polypeptide is cultivated using methods well known to one skilled in the art.

The embodiments provide compositions for screening compounds that modulate expression within plants. The vectors, cells, and plants can be used for screening candidate molecules for agonists and antagonists of the 2OD oxygenase promoter. For example, a reporter gene can be operably linked to a 2OD oxygenase promoter and expressed as a transgene in a plant. Compounds to be tested are added and reporter gene expression is measured to determine the effect on promoter activity.

The following examples are offered by way of illustration and not by way of limitation.

EXPERIMENTAL

The embodiments are further defined in the following Examples, in which parts and percentages are by weight and degrees are Celsius, unless otherwise stated. Techniques in molecular biology were typically performed as described in Ausubel or Sambrook, supra. It should be understood that these Examples, while indicating embodiments of the invention, are given by way of illustration only. From the above discussion and these Examples, one skilled in the art can ascertain the essential characteristics of the embodiments, and without departing from the spirit and scope thereof, can make various changes and modifications of them to adapt to various usages and conditions. Thus, various modifications of the embodiments in addition to those shown and described herein will be apparent to those skilled in the art from the foregoing description. Such modifications are also intended to fall within the scope of the appended claims.

The disclosure of each reference set forth herein is incorporated herein by reference in its entirety.

EXAMPLE 1

Identification of the 2OD Oxygenase Gene

The oxygenase gene was identified using Massively Parallel Signature Sequencing technology (MPSS) (see Brenner S, et al. (2000) *Nature Biotechnology* 18:630–634, Brenner S et al. (2000) *Proc Natl Acad Sci USA* 97:1665–1670). This technology involves the generation of 17 base signature tags from mRNA samples that have been reverse transcribed. The tags are simultaneously sequenced and assigned to genes or ESTs. The abundance of these tags is given a number value that is normalized to parts per million (PPM) which then allows the tag expression, or tag abundance, to be compared across different tissues. Thus, the MPSS platform can be used to determine the expression pattern of a particular gene and its expression level in different tissues.

Querying the MPSS database for signature tags that were preferentially upregulated in response to corn rootworm (CRW) feeding damage resulted in the identification of a tag corresponding to a maize 2OD oxygenase gene. The query identified root tag profiles from V5 staged maize plants treated with CRW. The query also identified root tag profiles from V6 stage plants undamaged by CRW. A comparison of the profiles showed the 2OD oxygenase tag was upregulated from 704 ppm to 2566 ppm in response to CRW feeding within 24 hours. A comparison made across all experiments and tissues in the MPSS database indicated the 2OD oxygenase gene was expressed preferentially in roots.

EXAMPLE 2

Induction of Oxygenase Gene Expression

Evidence that the oxygenase gene is expressed in an inducible manner was substantiated by northern blot analysis (FIG. 1). RNA was isolated from the nodal roots and the V5 leaf of V5 stage (5 collared leaves) B73 maize plants whose roots had been damaged by corn rootworm feeding on them for 24 hours. The results demonstrated that the 2OD oxygenase gene expression was strongly upregulated by CRW feeding damage. The induction was only observed in the roots. No induction was observed in the leaves.

To determine if insect feeding directly on leaf tissue might induce 2OD oxygenase expression, European corn borer were allowed to feed on V5 stage maize plants for 24 hours. Damage from the larvae did not upregulate expression in the whorl/leaf transition zone, as expression levels, determined by MPSS, were at background levels of 7 ppm.

In the corn rootworm feeding experiments, plants were either repotted, or not repotted, to determine whether this process caused any root damage that would induce expression of the oxygenase gene. Repotting refers to transplanting the plant into fresh soil. Root damage caused by this process did not induce 2OD oxygenase expression.

Mechanical wounding of the roots, specifically by crushing the root tips, does induce the oxygenase gene. MPSS results showed induction of the gene peaks at approximately 3 hours after the wound was administered. Expression then tapers off steadily to 24 hours, the last time point in the experiment. Similar results were obtained via northern blot analysis (FIG. 2). The root tips of V5 stage plants were mechanically wounded and the nodal roots and V5 leaf were harvested at 0, 2, 6, 12 and 24 hours post-wounding. Results showed expression peaked in the roots about 6 hours after wounding and then steadily declined to the 24 hour time point. No expression was detected in leaves during the experiment. Thus based on these data, the 2OD oxygenase gene is induced in roots, in a time frame of approximately 3–6 hours after wounding Taken together, the expression results show the oxygenase gene is up-regulated in response to CRW feeding and mechanical wounding of roots. The up regulation and expression is root preferred, making the promoter a suitable candidate to direct significant levels of transgene expression in plants, such as maize, in cases where insect or wound induction of transgene expression is desired.

Materials and Methods Utilized

Maize plants from the B73 line were grown under greenhouse conditions to the stage of V5 and infested with 75 $2^{nd}$ instar CRW larvae. Leaves (V5 leaf) and nodal roots were harvested after allowing the larvae to feed for 24 hours. Uninfested V5 stage plants were also sampled as controls for the experiments. RNA was extracted from the tissues using RNA Easy Maxi Kit (Qiagen, Valencia, Calif.)

The RNA samples were electrophoresed through a standard formaldehyde gel using Northern Max Denaturing Gel Buffers (Ambion, Austin, Tex.) Afterwards, the gel was washed once in 20×SSC for a total of 15 minutes, then blotted to a nylon membrane overnight in 20×SSC (Turboblotter from S&S). The membrane was UV-crosslinked for 2 minutes. Pre-hybridization of the blot totaled 3 hours at 50° C. in 15 mL DIG Easy Hyb Solution (Roche Applied Sciences, Indianapolis, Ind.) Single-stranded DNA probes were made from the 2OD oxygenase EST by PCR using the PCR DIG Probe Synthesis Kit (Roche). Following the kit protocol recommendations, 2 μL of denatured probe was added per 1 mL of DIG Easy Hyb solution. Hybridization was allowed to go overnight at 50° C. in 10 mL of solution. The next day the membrane was washed twice in low stringency buffer (2×SSC containing 0.1% SDS) at room temperature for 5 minutes, and then washed twice in high stringency buffer (0.1×SSC containing 0.1% SDS) at 55° C. for 15 minutes.

Visualization of the 2OD oxygenase transcripts was accomplished using the DIG OMNI System for PCR Probes and DIG Wash and Block Buffer Set from Roche. Briefly, the membrane was equilibrated in washing buffer (0.1M maleic acid, 0.15 M NaCl, pH 7.5; 0.3% (v\v) Tween 20) for 2 minutes at room temperature, then put in blocking solution (1:10 dilution of 10× blocking solution in maleic acid buffer (0.1M maleic acid, 0.15 M NaCl, pH 7.5)) for 30 minutes. The membrane was incubated in antibody solution (anti-DIG-alkaline phosphate diluted 1:10,000 in blocking solution (10× blocking solution diluted 1:10 in maleic acid buffer)) for 30 minutes and washed 2 times in washing buffer for a total of 30 minutes. After equilibration in detection buffer (0.1M Tris-HCl, 0.1M NaCl, pH 9.5) for 3 minutes, the membrane was placed in a plastic development folder (Applied BioSystems) and 1 mL of CDP-Star working solution (1:100 dilution of CDP-Star (25 mM, 12.38 mg/mL) in detection buffer) was applied drop-wise to the membrane. Following a 5 minute incubation at room temperature, the membrane was exposed to X-ray film from 20 minutes to overnight.

EXAMPLE 3

5' RACE Protocol to Identify Transcriptional Start Site

5' RACE was used to map the transcriptional start site for the 2OD oxygenase mRNA and was performed according to the protocol provided with the 5' RACE System for the Rapid Amplification of cDNA Ends (Invitrogen, Carlsbad, Calif.) using RNA isolated from roots of maize inbred B73 plants. Gene-specific primers (GSP) were designed to the 3'UTR of the 2OD oxygenase gene based on the identified EST sequence. The alternative protocol for GC-rich templates was followed using SuperScript II Reverse Transcriptase (supplied in the kit) for first strand synthesis using GSP1R (SEQ ID NO: 2) located on the complementary strand from +1321 to +1340 bp relative to the translation start site (ATG) of the 2OD oxygenase gene, and the general system protocol was followed for the subsequent steps of RNase treatment, reaction clean-up and dC-tailing of the cDNA. PCR amplification was performed with GSP2R (SEQ ID NO: 3), also located on the complementary DNA strand between +1252 and +1271 bp relative to the ATG, in combination with the Abridged anchor primer (supplied in the kit) using HotStarTaq Polymerase (Qiagen). The PCR conditions used were: 1 cycle of 95° C. for 15 min; followed by 35 cycles of the combination of 94° C. for 30 sec, 55° C. for 45 sec, and 72° C. for 1 min; and completed by 1 cycle of 72° C. for 10 min.

A second round of PCR was conducted using GSP3R (SEQ ID NO: 4) located on the complementary strand from +1141 to +1160 bp, with the kit supplied AUAP primer using the first round PCR products as templates. Second round PCR was performed with HotStarTaq DNA polymerase (Qiagen) using the following PCR conditions: 1 cycle of 95° C. for 15 min; followed by 35 cycles of 94° C. for 30 sec, 55° C. for 45 sec, and 72° C. for 1 min; and completed by 1 cycle of 72° C. for 10 min.

The 5' RACE products were TA-cloned into pCR2.1 (Invitrogen) and sequenced using M13 forward and reverse primers. The 5' RACE sequence identified the transcriptional start site for the 2OD oxygenase mRNA to be located −39 bp relative to the 2OD oxygenase translational (ATG) start site.

EXAMPLE 4

Isolation of the Promoter for the 2OD Oxygenase Gene and Sequence Analysis

Analysis of the 2OD oxygenase gene in Examples 1 and 2 indicated it was induced with mechanical wounding and insect feeding on the roots. Thus, the 2OD oxygenase promoter could be used to direct expression in maize plants subject to insect pest infestation or mechanical injury to the roots.

A promoter of approximately 1116 bp (SEQ ID NO 1) was isolated from the 2OD oxygenase gene. A putative TATA box was identified between −35 and −29 bp relative the 2OD oxygenase transcriptional start site (see FIG. 3). Two sequence motifs consisting of TTGAC corresponding to a "W-box" were identified at the distal end of SEQ ID NO 1. The "W-box" motif is recognized by salicylic acid-induced WRKY-DNA binding proteins in response to environmental stresses (Chen et al., 2002, Plant Cell. 14: 559–574).

The sequence was isolated using multiple reiterative BLASTN searches of the Genome Survey Sequence (GSS) database based on EST sequence from two EST clones. Each search of the GSS database used available sequence obtained from the previous search to "walk" along genomic sequence until no further overlapping sequence was identified. GSS searching resulted in 597 bp of sequence upstream of the 2OD oxygenase transcriptional start site. An additional 486 bp of sequence upstream of the GSS-derived sequence was obtained by genome walking as described below.

Using the sequence obtained from the GSS database search, Genome Walking reactions were performed to obtain more upstream flanking sequence. Reactions were done using the Universal Genome Walker Kit from Clontech/BD Biosciences (Palo Alto, Calif.) Genomic DNA libraries were constructed according to the kit protocol using B73 genomic DNA. PCR reactions were performed using Platinum Pfx DNA Polymerase (Invitrogen), and cycling conditions in Appendix C: for GeneAmp System 9600 were used. First round reactions were done using GSP1GW (SEQ ID NO: 5) corresponding to complementary strand between −362 bp to −336 bp from the 2OD oxygenase translational start site and the AP1 primer (supplied in kit). Second round reactions were performed using product from the first round as template and either GSP2GW (SEQ ID NO: 6) or GSP3GW (SEQ ID NO: 7) with the AP2 (supplied in kit). GSP2GW and GSP3GW correspond to the complementary stand between −442 bp and −416 bp and between −468 bp and −440 bp relative to the translational start site, respectively. DNA resulting from the second round reactions was cloned into the TA vector pCR2.1 (Invitrogen) and sequenced.

The 2OD oxygenase promoter was isolated by PCR on genomic DNA using Platinum Pfx DNA Polymerase (Invitrogen) in 2× buffer and oligonucleotide primers, OligoXbaI (SEQ ID NO: 8) and OligoBamHINcoI (SEQ ID NO: 9). Restriction enzyme sites corresponding to XbaI and NcoI and BamHI were added to facilitate subsequent cloning. PCR conditions used were 1 cycle of 95° C. for 5 min; followed by 35 cycles of 94° C. for 30 sec, 60° C. for 45 sec, and 68° C. for 2 min; and completed by 1 cycle of 68° C. for 10 min.

EXAMPLE 5

Activity of the 2OD Oxygenase Promoter

To demonstrate that the DNA sequence isolated as the 2OD oxygenase promoter functions as a promoter, transient particle bombardment assays were performed. These assays provided a rapid assessment of whether the DNA sequence tested is able to direct gene expression.

The 1116 bp promoter was PCR amplified from genomic DNA and cloned into an expression vector in front of the B-glucuronidase (GUS) gene to test whether the promoter would direct expression. Biolistic bombardment of 3-day-old maize seedlings with this expression cassette resulted in GUS staining foci on the coleoptile. The level of staining was less than the control, which consisted of the strong, constitutive root promoter, Rootmetpro2 (See U.S. patent application Ser. No. 11/022,449), directing GUS expression. These results indicate that the 1116 bp 2OD oxygenase promoter is able to direct expression in transiently transformed maize cells.

Materials and Methods Utilized for the Biolistic Transient Root Expression Assay B73 seeds were placed along the edge of a sheet of germination paper previously soaked in a 7% sucrose solution. An additional sheet of germination paper identical in size to the first was soaked in 7% sucrose and used to overlay the seeds. The germination paper—kernel—germination paper sandwich was subsequently rolled and placed into a beaker of 7% sucrose solution, such that the solution would wick up the paper to the kernels at the top of the roll. This process allowed for straight root growth. Kernels were permitted to germinate and develop for 2–3 days in the dark at 27–28° C. Prior to bombardment, the outer sheath covering the coleoptile was removed and then the seedlings were placed in a sterile petri dish (60 mm) on a layer of Whatman #1 filter paper moistened with 1 mL of $H_2O$. Two seedlings per plate were arranged in opposite orientations and anchored to the filter paper with a 0.5% agarose solution.

DNA/gold particle mixtures were prepared for bombardment in the following method. Sixty mg of 0.6–1.0 micron gold particles were pre-washed with ethanol, rinsed with sterile distilled $H_2O$, and resuspended in a total of 1 mL of sterile $H_2O$. 50 μL aliquots of gold particle suspension were stored in siliconized Eppendorf tubes at room temperature. DNA was precipitated onto the surface of the gold particles by combining, in order, 50 μL of pre-washed 0.6 μM gold particles, 5–10 µg of test DNA, 50 µL 2.5 M $CaCl_2$ and 25 µL of 0.1 M spermidine. The solution was immediately vortexed for 3 minutes and centrifuged briefly to pellet the DNA/gold particles. The DNA/gold was washed once with 500 µL of 100% ethanol and suspended in a final volume of 50 µL of 100% ethanol. The DNA/gold solution was incubated at −20° C. for at least 60 minutes prior to applying 6 µL of the DNA/gold mixture onto each Mylar™ macrocarrier.

Seedlings, prepared as indicated above, were bombarded with DNA/gold particles twice using the PDS-1000/He gun at 1100 psi under 27–28 inches of Hg vacuum. The distance between macrocarrier and stopping screen was between 6–8 cm. Plates were incubated in sealed containers for 24 hours in the dark at 27–28° C. following bombardment.

After 18 to 24 hours of incubation, the bombarded seedlings were assayed for transient GUS expression. Seedlings were immersed in 10–15 mL of GUS assay buffer containing 100 mM $NaH_2PO_4$—$H_2O$ (pH 7.0), 10 mM EDTA, 0.5 mM $K_4Fe(CN)_6$-$3H_2O$, 0.1% Triton X-100 and 2 mM 5-bromo-4-chloro-3-indoyl glucuronide. The seedlings were incubated in the dark for 24 hours at 37° C. Replacing the GUS staining solution with 100% ethanol stopped the assay. GUS expression/staining was visualized under a microscope.

EXAMPLE 6

Expression of 2OD Oxygenase in Transgenic Plants

Stable transformed plants were created using *Agrobacterium* transformation protocols as per Example 8, to allow for a more detailed characterization of promoter activity, including induction of the promoter via mechanical wounding and wounding via insect feeding.

The 1116 bp 2OD oxygenase promoter (SEQ ID NO: 1) was operably linked to the Adh1 intron and the GUS gene (abbreviated as 2OD oxygenase(Adh1 intron1):GUS) which allowed for the detection of promoter activity by histochemically staining plant tissues for GUS enzymatic activity. The pattern of GUS staining reflects where the promoter is active. The Adh1 intron was included for the purpose of increasing expression as it has been shown in cereal cells that the expression of foreign genes is enhanced by the presence of an intron in gene constructions (See Callis et al. (1987) *Genes and Development* 1: 1183–1200; Kyozuka et al. (1990) *Maydica* 35:353–357).

V5 stage plants (5 collared leaves) were evaluated under normal growing conditions, under stress by wounding or under CRW feeding pressure. Wounding the nodal roots of the 2OD oxygenase plants was accomplished by crushing approximately 1 inch of the root tip with serrated pliers and waiting 24 hours before sampling the tissue. CRW infestation was accomplished by placing approximately 100 $2^{nd}$ instar CRW larvae beneath the root mass in the pot. Leaf and root material was collected 48 hours later. Plants assessed prior to treatment (i.e. under normal greenhouse growth conditions) provided a baseline by which to gauge induction with each treatment, Expression was absent in most of the greenhouse plants without any treatment. However, wounding resulted in expression. Each of the plants showed induction of GUS expression. Interestingly, the expression was localized to the wound site and was not detected adjacent to the wound nor in portions of the root upstream of the wound.

The localized response was also indicative of CRW feeding. GUS expression was observed in root tissue at or near where CRW had damaged or tunneled through the root. But unlike the mechanically wounded roots, expression in the CRW fed roots could be detected beyond the tip and into the mature regions of the root. No expression was detected in the leaves of these plants, similar to what was observed in the leaves from mechanically wounded plants. Taken together, the results indicate the 2OD oxygenase promoter is inducible in the roots of transgenic plants.

R1–R2 stage plants (denoted by silking and pollen shed) were characterized for 2OD directed expression in pollen, tassels, and silks. In pollen, no expression was observed from any of the plants. However in tassels, GUS histochemical analysis revealed that approximately half of the plants sampled stained for GUS activity. The level of staining in the tissues tended to be low and in comparison to the level of staining in the roots, expression in the tassels was at or below the level in roots. For silks, all but one event showed some level of GUS expression. Expression was not in all strands, but rather in approximately 5 to 50% of the strands in each sample. The expression was mostly in the veins with inconsistent staining throughout the silk strand.

Histochemical Staining of Plant Tissues for GUS Activity

Detection of GUS activity was accomplished by placing tissue from transformed plants into 48-well, 12-well or 6-well plates containing 0.5 to 5 mL GUS assay buffer (assay buffer recipe described in Example 5). Plates were placed under house vacuum for 10 min, and then incubated overnight at 37° C. Tissue was cleared of pigmentation with 1 to 3 successive 12 hour incubations in 100% ethanol at room temperature. The tissues were stored in 70% ethanol at 4° C.

EXAMPLE 8

*Agrobacterium*-Mediated Transformation of Maize and Regeneration of Transgenic Plants For *Agrobacterium*-mediated transformation of maize with a 2OD oxygenase promoter sequence of the embodiments, the method of Zhao was employed (U.S. Pat. No. 5,981,840, (hereinafter the '840 patent) and PCT patent publication WO98/32326; the contents of which are hereby incorporated by reference).

*Agrobacterium* were grown on a master plate of 800 medium and cultured at 28° C. in the dark for 3 days, and thereafter stored at 4° C. for up to one month. Working plates of Agrobacterium were grown on 810 medium plates and incubated in the dark at 28° C. for one to two days.

Briefly, embryos were dissected from fresh, sterilized corn ears and kept in 561Q medium until all required embryos were collected. Embryos were then contacted with an *Agrobacterium* suspension prepared from the working plate, in which the *Agrobacterium* contained a plasmid comprising the promoter sequence of the embodiments. The embryos were co-cultivated with the *Agrobacterium* on 562P plates, with the embryos placed axis down on the plates, as per the '840 patent protocol.

After one week on 562P medium, the embryos are transferred to 563O medium. The embryos are subcultured on fresh 563O medium at 2 week intervals and incubation is continued under the same conditions. Callus events begin to appear after 6 to 8 weeks on selection.

After the calli reach the appropriate size, the calli are cultured on regeneration (288W) medium and are kept in the dark for 2–3 weeks to initiate plant regeneration. Following somatic embryo maturation, well-developed somatic embryos are transferred to medium for germination (272V)

and transferred to a lighted culture room. Approximately 7–10 days later, developing plantlets are transferred to 272V hormone-free medium in tubes for 7–10 days until plantlets are well established. Plants are then transferred to inserts in flats (equivalent to 2.5" pot) containing potting soil and grown for 1 week in a growth chamber, subsequently grown an additional 1–2 weeks in the greenhouse, then transferred to classic 600 pots (1.6 gallon) and grown to maturity.

Media Used in *Agrobacterium*-Mediated Transformation and Regeneration of Transgenic Maize Plants:

561Q medium comprises 4.0 g/L N6 basal salts (SIGMA C-1416), 1.0 mL/L Eriksson's Vitamin Mix (1000× SIGMA-1511), 0.5 mg/L thiamine HCl, 68.5 g/L sucrose, 36.0 g/L glucose, 1.5 mg/L 2,4-D, and 0.69 g/L L-proline (brought to volume with dl $H_2O$ following adjustment to pH 5.2 with KOH); 2.0 g/L Gelrite™ (added after bringing to volume with dl $H_2O$); and 8.5 mg/L silver nitrate (added after sterilizing the medium and cooling to room temperature).

800 medium comprises 50.0 mL/L stock solution A and 850 mL dl $H_2O$, and brought to volume minus 100 mL/L with dl $H_2O$, after which is added 9.0 g of phytagar. After sterilizing and cooling, 50.0 mL/L stock solution B is added, along with 5.0 g of glucose and 2.0 mL of a 50 mg/mL stock solution of spectinomycin. Stock solution A comprises 60.0 g of dibasic $K_2HPO_4$ and 20.0 g of monobasic sodium phosphate, dissolved in 950 mL of water, adjusted to pH 7.0 with KOH, and brought to 1.0 L volume with dl $H_2O$. Stock solution B comprises 20.0 g $NH_4Cl$, 6.0 g $MgSO_4.7H_2O$, 3.0 g potassium chloride, 0.2 g $CaCl_2$, and 0.05 g of $FeSO_4.7H_2O$, all brought to volume with dl $H_2O$, sterilized, and cooled.

810 medium comprises 5.0 g yeast extract (Difco), 10.0 g peptone (Difco), 5.0 g NaCl, dissolved in dl $H_2O$, and brought to volume after adjusting pH to 6.8. 15.0 g of bacto-agar is then added, the solution is sterilized and cooled, and 1.0 mL of a 50 mg/mL stock solution of spectinomycin is added.

562P medium comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, and 2.0 mg/L 2,4-D (brought to volume with dl $H_2O$ following adjustment to pH 5.8 with KOH); 3.0 g/L Gelrite™ (added after bringing to volume with dl $H_2O$); and 0.85 mg/L silver nitrate and 1.0 mL of a 100 mM stock of acetosyringone (both added after sterilizing the medium and cooling to room temperature).

5630 medium comprises 4.0 g/L N6 basal salts (SIGMA C-1416), 1.0 mL/L Eriksson's Vitamin Mix (1000× SIGMA-1511), 0.5 mg/L thiamine HCl, 30.0 g/L sucrose, 1.5 mg/L 2,4-D, 0.69 g L-proline, and 0.5 g MES buffer (brought to volume with dl $H_2O$ following adjustment to pH 5.8 with KOH). Then, 6.0 g/L Ultrapure™ agar-agar (EM Science) is added and the medium is sterilized and cooled. Subsequently, 0.85 mg/L silver nitrate, 3.0 mL of a 1 mg/mL stock of Bialaphos, and 2.0 mL of a 50 mg/mL stock of carbenicillin are added.

288 W comprises 4.3 g/L MS salts (GIBCO 11117-074), 5.0 mL/L MS vitamins stock solution (0.100 g nicotinic acid, 0.02 g/L thiamine HCl, 0.10 g/L pyridoxine HCl, and 0.40 g/L Glycine brought to volume with polished D-I $H_2O$) (Murashige and Skoog (1962) *Physiol. Plant.* 15:473), 100 mg/L myo-inositol, 0.5 mg/L zeatin, and 60 g/L sucrose, which is then brought to volume with polished D-I $H_2O$ after adjusting to pH 5.6. Following, 6.0 g/L of Ultrapure™ agar-agar (EM Science) is added and the medium is sterilized and cooled. Subsequently, 1.0 mL/L of 0.1 mM abscisic acid; 1.0 mg/L indoleacetic acid and 3.0 mg/L Bialaphos are added, along with 2.0 mL of a 50 mg/mL stock of carbenicillin.

Hormone-free medium (272V) comprises 4.3 g/L MS salts (GIBCO 11117-074), 5.0 mL/L MS vitamins stock solution (0.100 g/L nicotinic acid, 0.02 g/L thiamine HCl, 0.10 g/L pyridoxine HCl, and 0.40 g/L Glycine brought to volume with polished dl $H_2O$), 0.1 g/L myo-inositol, and 40.0 g/L sucrose (brought to volume with polished dl $H_2O$ after adjusting pH to 5.6); and 6 g/L Bacto-agar (added after bringing to volume with polished dl $H_2O$), sterilized and cooled to 60° C.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

The invention claimed is:

1. An isolated nucleic acid molecule comprising a nucleotide sequence selected from the group consisting of:
 a) a nucleotide sequence comprising the sequence set forth in SEQ ID NO: 1 or the full length complement thereof;
 b) a nucleotide sequence comprising a fragment of SEQ ID NO: 1, wherein said fragment has promoter activity; and
 c) a nucleotide sequence comprising the plant promoter sequence of the plasmid deposited as Patent Deposit No. PTA-6278, or the full length complement thereof.

2. A DNA construct comprising the nucleic acid molecule of claim 1 operably linked to a heterologous nucleotide sequence of interest.

3. A vector comprising the DNA construct of claim 2.

4. A plant cell having stably incorporated into its genome the DNA construct of claim 2.

5. The plant cell of claim 4, wherein said plant cell is from a monocot.

6. The plant cell of claim 5, wherein said monocot is maize.

7. The plant cell of claim 4, wherein said plant cell is from a dicot.

8. A plant having stably incorporated into its genome the DNA construct of claim 2.

9. The plant of claim 8, wherein said plant is a monocot.

10. The plant of claim 9, wherein said monocot is maize.

11. The plant of claim 8, wherein said plant is a dicot.

12. A transgenic seed of the plant of claim 8, wherein the seed comprises the DNA construct.

13. The plant of claim 8, wherein the heterologous nucleotide sequence of interest encodes a gene product that confers herbicide, salt, cold, drought, pathogen, or insect resistance.

14. A method for expressing a nucleotide sequence in a plant, said method comprising introducing into a plant a DNA construct, said DNA construct comprising a promoter and operably linked to said promoter a heterologous nucleotide sequence of interest, wherein said promoter comprises a nucleotide sequence selected from the group consisting of:
 a) a nucleotide sequence comprising the sequence set forth in SEQ ID NO: 1;
 b) a nucleotide sequence comprising a fragment of SEQ ID NO: 1 wherein said fragment has promoter activity; and
 c) a nucleotide sequence comprising the plant promoter sequence of the plasmid designated as Patent Deposit No. PTA-6278;
and expressing said heterologous nucleotide sequence.

15. The method of claim 14, wherein said plant is a dicot.

16. The method of claim 14, wherein said plant is a monocot.

17. The method of claim 16, wherein said monocot is maize.

18. The method of claim 14, wherein the heterologous nucleotide sequence encodes a gene product that confers herbicide, salt, cold, drought, pathogen, or insect resistance.

19. The method of claim 14, wherein said heterologous nucleotide sequence of interest is selectively expressed in the root.

20. A method for expressing a nucleotide sequence in a plant cell, said method comprising introducing into a plant cell a DNA construct comprising a promoter operably linked to a heterologous nucleotide sequence of interest, wherein said promoter comprises a nucleotide sequence selected from the group consisting of:
   a) a nucleotide sequence comprising the sequence set forth in SEQ ID NO: 1;
   b) a nucleotide sequence comprising a fragment of SEQ ID NO: 1 wherein said fragment has promoter activity, and
   c) a nucleotide sequence comprising the plant promoter sequence of the plasmid designated as Patent Deposit No. PTA-6278;
and expressing heterologous nucleotide sequence.

21. The method of claim 20, wherein said plant cell is from a monocot.

22. The method of claim 21, wherein said monocot is maize.

23. The method of claim 20, wherein said plant cell is from a dicot.

24. The method of claim 20, wherein the heterologous nucleotide sequence encodes a gene product that confers herbicide, salt, cold, drought, pathogen, or insect resistance.

25. A method for selectively expressing a nucleotide sequence in a plant root, said method comprising introducing into a plant cell a DNA construct, regenerating a transformed plant from said plant cell, said DNA construct comprising a promoter and a heterologous nucleotide sequence operably linked to said promoter, wherein said promoter comprises a nucleotide sequence selected from the group consisting of:
   a) a nucleotide sequence comprising the sequence set forth in SEQ ID NO: 1;
   b) a nucleotide sequence comprising a fragment of SEQ ID NO: 1 wherein said fragment has promoter activity; and
   c) a nucleotide sequence comprising the plant promoter sequence of the plasmid deposited as Patent Deposit No. PTA-6278;
and expressing said heterologous nucleotide sequence.

26. The method of claim 25, wherein expression of said heterologous nucleotide sequence alters the phenotype of said plant.

27. The method of claim 25, wherein the plant is a monocot.

28. The method of claim 27, wherein the monocot is maize.

29. The method of claim 25, wherein the plant is a dicot.

30. The method of claim 25, wherein the heterologous nucleotide sequence encodes a gene product that confers herbicide, salt, cold, drought, pathogen, or insect resistance.

* * * * *

SEQUENCE LISTING

<160> NUMBER OF SEQ ID NOS: 9

<210> SEQ ID NO 1
<211> LENGTH: 1116
<212> TYPE: DNA
<213> ORGANISM: Zea mays

<400> SEQUENCE: 1

```
gtcgacatgt cacgttatca atgtagagac tgataaaaat ttgactctgt ttcgtgaaag      60
ttgacatgca ctatgtgtag aaacctagcc ggccttcaca tgaaatcata aaacttctac     120
ggaggtcggc taggtttgta tacacaacac tcgacaaaga aggcatatct ggaaaccgat     180
atggcttttt tttataagtg ttgtagtcct gacactcgac aaagaagctc catttgccga     240
```

```
gtgcctccca gcacacttgg caaagtgact ggcaaagggg cccactattg ccccctttgt    300
cgagagtgcc aggctggcag tcactcgaca aagatgctcc ctttgccaag tgtcaattgc    360
ggctctcggc acaaaggctg tcgtgggggc ccactggagc cttatttgcc gagtgtcacg    420
ccagcaggca ctcgataaag gcttcctttt tgccgagtgc cattgaggac actcgacata    480
gtctctgtca ccatcacttg tcgctgtcac ggcaattttt ctttgccgag cactagggga    540
cacttggtaa agactttgcc gagtgtccga cataatgcta tcggtaaaga ggtcgttgct    600
gatgtacagt tcactgagtc cttttttacta agtgtcacac tcgacaaaga gtttgttgag    660
tgttttttag gctttgccga gtgcttgcga cactcggcaa agcagtatgt tttggtagtg    720
aggtcgttgt cgataaacag ttcaccgatc cctatttgcc gaatgctaca ctcgaagtgc    780
cgcaggcact cgggaaagaa ccctgtttcg gttgtgactt ggtattgtta ggctgtgtat    840
tgaatccaat gctatcacat tagatataaa ctagataacc gcgtatacag tgttttattc    900
gataaaactc taccctctcc tatgaaactg tctctatatc tttcctctta attacagtca    960
tgttccgcac atgatgctgt atcaccgcac atggagagag agaaaaatag attggtcagg   1020
ctgtttgtat atgcaaggcc tacgcttcta tttaaagacc gtatcgtggt tgcaggcaga   1080
agcacacaag ctagcaattg aaaaaaaaaa caggca                             1116
```

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide Primer GSP1R

<400> SEQUENCE: 2

```
cacaaaggta ccacacacac                                                 20
```

<210> SEQ ID NO 3
<211> LENGTH: 20
<212> TYPE: DNA
<213> ORGANISM: Artificial Sequence
<220> FEATURE:
<223> OTHER INFORMATION: Oligonucleotide Primer GSP2R

<400> SEQUENCE: 3

```
tctgcggatg aagggaatgg                                                 20
```

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide Primer GSP3R

<400> SEQUENCE: 4

```
caagactaga cgtggtgtgc                                                 20
```

<210> SEQ ID NO 5
<211> LENGTH: 27
<212> TYPE: DNA
<213> ORGANISM: Artificial Sequence
<220> FEATURE:
<223> OTHER INFORMATION: Oligonucleotide Primer GSP1GW

<400> SEQUENCE: 5

```
gcctgcggca cttcgagtgt agcattc                                         27
```

-continued

```
<210> SEQ ID NO 6
<211> LENGTH: 27
<212> TYPE: DNA
<213> ORGANISM: Artificial Sequence
<220> FEATURE:
<223> OTHER INFORMATION: Oligonucleotide Primer GSP2GW

<400> SEQUENCE: 6
tactgctttg ccgagtgtcg caagcac                                27

<210> SEQ ID NO 7
<211> LENGTH: 29
<212> TYPE: DNA
<213> ORGANISM: Artificial Sequence
<220> FEATURE:
<223> OTHER INFORMATION: Oligonucleotide Primer GSP3GW

<400> SEQUENCE: 7
cactcggcaa agcctaaaaa acactcaac                              29

<210> SEQ ID NO 8
<211> LENGTH: 29
<212> TYPE: DNA
<213> ORGANISM: Artificial Sequence
<220> FEATURE:
<223> OTHER INFORMATION: Oligonucleotide Primer OligoXbaI

<400> SEQUENCE: 8
cgcgtctaga gtcgacatgt cacgttatc                              29

<210> SEQ ID NO 9
<211> LENGTH: 26
<212> TYPE: DNA
<213> ORGANISM: Artificial Sequence
<220> FEATURE:
<223> OTHER INFORMATION: Oligonucleotide Primer OligoBamHINcoI

<400> SEQUENCE: 9
gcggtcggag ccatggatcc tgcctg                                 26
```